(12) United States Patent
Fu et al.

(10) Patent No.: US 9,688,984 B2
(45) Date of Patent: Jun. 27, 2017

(54) SPL16 COMPOSITIONS AND METHODS TO INCREASE AGRONOMIC PERFORMANCE OF PLANTS

(71) Applicant: Institute of Genetics and Developmental Biology, Beijing (CN)

(72) Inventors: Xiangdong Fu, Beijing (CN); Shaokui Wang, Beijing (CN); Kun Wu, Beijing (CN); Guiquan Zhang, Beijing (CN); Ruizhen Zeng, Beijing (CN)

(73) Assignee: INSTITUTE OF GENETICS AND DEVELOPMENTAL BIOLOGY, Beijing (CN)

( * ) Notice: Subject to any disclaimer, the term of this patent is extended or adjusted under 35 U.S.C. 154(b) by 372 days.

(21) Appl. No.: 14/347,911

(22) PCT Filed: Sep. 19, 2012

(86) PCT No.: PCT/CN2012/081597
§ 371 (c)(1),
(2) Date: Mar. 27, 2014

(87) PCT Pub. No.: WO2013/044742
PCT Pub. Date: Apr. 4, 2013

(65) Prior Publication Data
US 2014/0237685 A1    Aug. 21, 2014

(30) Foreign Application Priority Data
Sep. 30, 2011    (CN) .......................... 2011 1 0294864

(51) Int. Cl.
C12N 15/113    (2010.01)
C12N 15/82    (2006.01)
C07K 14/415    (2006.01)
A01H 5/10    (2006.01)
C12Q 1/68    (2006.01)

(52) U.S. Cl.
CPC ............. *C12N 15/113* (2013.01); *A01H 5/10* (2013.01); *C07K 14/415* (2013.01); *C12N 15/8218* (2013.01); *C12N 15/8261* (2013.01); *C12Q 1/6895* (2013.01)

(58) Field of Classification Search
None
See application file for complete search history.

(56) References Cited

U.S. PATENT DOCUMENTS

2011/0126316 A1*    5/2011    Yu .................... C07K 14/415
                                                800/279

FOREIGN PATENT DOCUMENTS

| CN | 101161675 A | 4/2008 |
| CN | 101475939 A | 7/2009 |
| WO | 2009135130 A2 | 11/2009 |
| WO | WO 2009/135130 A2 * | 11/2009 |

OTHER PUBLICATIONS

Jiang et al., 2010, International Journal of Biological Sciences 6: 228-251.*
Agrawal et al., 2003, Microbiology and Molecular Biology Reviews 67: 657-685.*
Oryza sativa Indica Group cultivar Huajingxian74 squamosa promoter binding protein-like 16 (SPL16) gene, SPL16-GW8 allele, GenBank accession No. JX867117, published Dec. 15, 2012.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Wang et al., 2011, Theor. Appl. Genet. 122: 1489-1496.*
Xie et al., 2006, Plant Physiology 142: 280-293.*
Fan et al., 2006, Theor. Appl. Genet. 112: 1164-1171.*
Eamens et al., 2008, Plant Physiology 147: 456-468.*
Maniatis et al., Molecular Cloning: A Laboratory Manual, Cold Spring Harbor Laboratory, 1982, pp. 324-343 and 387-389.*
Wang, et al.; "Study of the Cultivation Technique of Good Quality Rice Variety-Huajinxuan 74"; Journal of Anhui Agricultural Sciences (2000) 28(5):583-584.

* cited by examiner

*Primary Examiner* — David T Fox
*Assistant Examiner* — Bratislav Stankovic
(74) *Attorney, Agent, or Firm* — Ballard Spahr LLP

(57) ABSTRACT

Methods and compositions that affect grain shape, width, and yield in rice are disclosed. Methods of transgenic modulation and marker-assisted breeding methods improve grain length to width ratio and grain yield in rice. Down-regulation of OsSPL16 in rice resulted in increased grain quality.

2 Claims, 14 Drawing Sheets

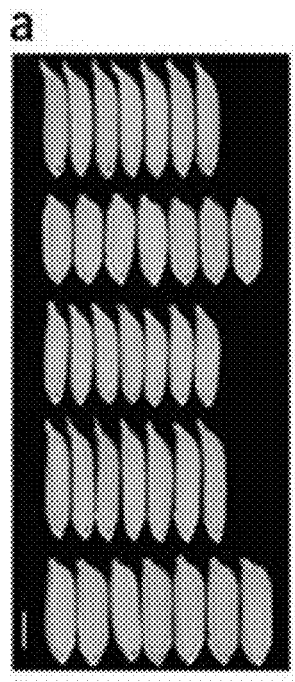
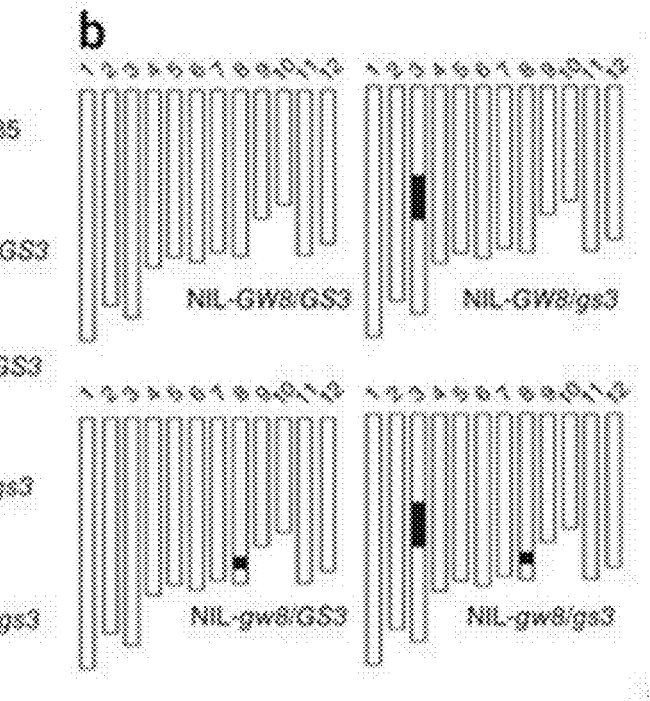
FIG. 11A  FIG. 11B
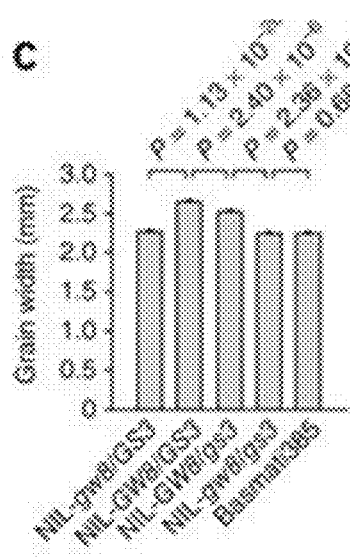
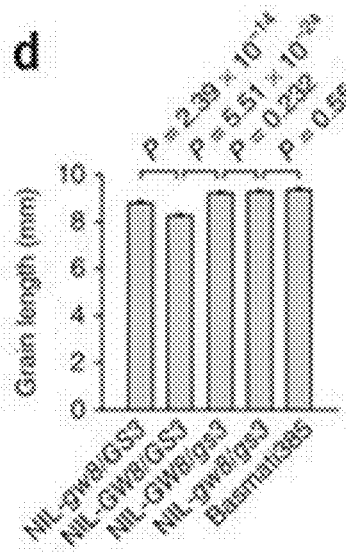
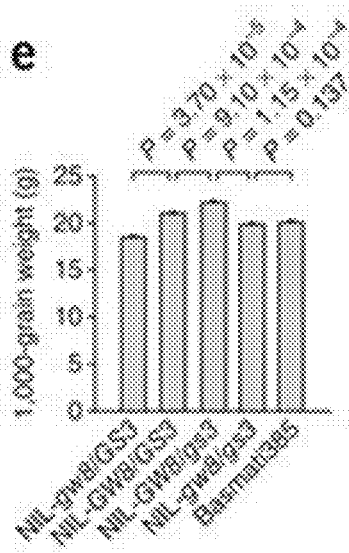
FIG. 11C  FIG. 11D  FIG. 11E

SEQUENCE LISTING

```
<160> NUMBER OF SEQ ID NOS: 47

<210> SEQ ID NO 1
<211> LENGTH: 1365
<212> TYPE: DNA
<213> ORGANISM: Oryza sativa

<400> SEQUENCE: 1
atggagtggg atctcaagat gccgccggcg gcgagttggg agctagccga cgagctggag      60
aacagcggcg gcggggtgt accggcggcg gtatcgtcgt catcggctgc ggttggtggc      120
ggcgtcaatg cggggggtgg tggcaggcag gagtgctcgg tcgacctcaa gctcggcggg      180
ttgggggagt tcggcggcgg cggcgcgcag ccgcgggtcg ccgtggcggg cgagctggcc      240 aagggaagg ggccagcggc cgccgccacg ggagcagcag cagcagcgtc gtcggcgccg      300
gcgaagcggc cgcgcggtgc ggcggcgggg cagcagcagt gcccgtcgtg cgcggtggac      360
gggtgcaagg aggacctgag caagtgccgc gactaccatc gccggcacaa ggtgtgcgag      420
gcccactcca agacccccct cgtcgtcgtc tccggccgcg agatgcgctt ctgccagcag      480
tgcagcaggt ttcacttgct tcaggagttt gatgaggcca agcgcagctg tagaaagcga      540
ctagatgggc acaaccgtcg ccgcaggaag ccacagccaa atcccatgaa ctctgcaagt      600
tatcttgcaa gccaacaagg ggcaagattc tcaccgttcg cgacgccgag accggaggca      660
agctggacag ggatgatcaa aaccgaggag agcccatact acacgcacca ccaaatccct      720
cttggcatca gcagcaggca gcagcatttc gttggctcca cctctgacgg cggccgccgc      780 ttcccttcc tccaggaagg cgagatcagc ttcggcaacg gcgccggcgc cggcggcgtg      840
ccaatggatc aggcagcagc tgctgctgct gcttcagtgt gccagccact tctgaagacg      900
gtagctcctc ctcctcctcc tcatggcggc ggcggcagcg gcggcggcaa gatgttctcc      960
gatggtgggt tgacacaagt gctcgactcc gattgtgctc tctctcttct gtcagctccg     1020
gcgaactcca cggccatcga cgtcggcggt ggccgggtgg tcgtccagcc gaccgagcac     1080
atccccattg cgcagcctct catctctggc cttcagttcg gcggcggcgg cggcagctca     1140
gcctggttcg cggcgcggcc gcatcatcag gcggccaccg gcgccgccgc caccgccgtc     1200
gtcgtctcga cggccggttt ctcctgcccg gtggtggaga gcgagcagct gaacacagtc     1260
ctgagctcca atgacaatga gatgaactac aatgggatgt tcacgtcgg cggcgaaggc     1320 tcatcggatg gcacgtcgtc gtctctgccg ttctcatggc agtag                     1365

<210> SEQ ID NO 2
<211> LENGTH: 1368
<212> TYPE: DNA
<213> ORGANISM: Oryza sativa
```

<400> SEQUENCE: 2

```
atggagtggg atctcaagat gccgccggcg gcgagctggg agctagccga cgagctggag      60
aacagcggcg gcggggtgt accggcggcg gtatcgtcgt catcggctgc ggttggtggc      120
ggcgtcaatg cggggggtgg tggcaggcag gagtgctcgg tcgacctcaa gctcggcggg     180
ttgggggagt tcggcggcgg cggcgcgcag ccgcgggtcg ccgtggcggg cgagccggcc     240
aaggggaagg ggccagcggc cgccgccacg ggagcagcag cagcagcgtc gtcggcgccg     300
gcgaagcggc cgcgcggtgc ggcggcggcg gggcagcagc agtgcccgtc gtgcgcggtg     360
gacgggtgca aggaggacct gagcaagtgc cgcgactacc atcgccggca caaggtgtgc     420
gaggcccact ccaagacccc cctcgtcgtc gtctccggcc gcgagatgcg cttctgccag     480
cagtgcagca ggtttcactt gcttcaggag tttgatgagg ccaagcgcag ctgtagaaag     540
cgactagatg ggcacaaccg tcgccgcagg aagccacagc cagatcccat gaactctgca     600
agttatcttg caagccaaca aggggcaaga ttctcaccgt tcgcgacgcc gagaccggag     660
gcaagctgga cagggatgat caaaaccgag gagagcccat actacacgca ccaccaaatc     720
cctcttggca tcagcagcag gcagcagcat ttcgttggct ccacctctga cggcggccgc     780
cgcttccctt cctccagga aggcgagatc agcttcggca ccggcgccgg cgccggcggc     840
gtgccaatgg atcaggcagc agctgctgct gctgcttcag tgtgccagcc acttctgaag     900
acggtagctc ctcctcctcc tcctcatggc ggcggcggca gcggcggcgg caagatgttc     960
tccgatggtg ggttgacaca agtgctcgac tccgattgtg ctctctctct tctgtcagct    1020
ccggcgaact ccacggccat cgacgtcggc ggtggccggg tggtcgtcca gccgaccgag    1080
cacatcccca tggcgcagcc tctcatctct ggccttcagt tcggcggcgg cggcggcagc    1140
tcagcctggt tcgcggcgcg gccgcatcat caggcggcca ccggcgccgc cgccaccgcc    1200
gtcgtcgtct cgacggccgg tttctcctgc ccggtggtgg agagcgagca gctgaacaca    1260
gtcctgagct ccaatgacaa tgagatgaac tacaatggga tgtttcacgt cggcggcgaa    1320
ggctcatcgg atggcacgtc gtcgtctctg ccgttctcat ggcagtag                 1368
```

<210> SEQ ID NO 3
<211> LENGTH: 1367
<212> TYPE: DNA
<213> ORGANISM: Oryza sativa

<400> SEQUENCE: 3

```
atggagtggg atctcaagat gccgccggcg gcgagctggg agctagccga cgagctggag      60
aacagcggcg gcggggtgt accggcggcg gtatcgtcgt catcggctgc ggttggtggc      120
ggcgtcaatg cggggggtgg tggcaggcag gagtgctcgg tcgacctcaa gctcggcggg     180
ttgggggagt tcggcggcgg cggcgcgcag ccgcgggtcg ccgtggcggg cgagctggcc     240
aaggggaagg ggccagcggc cgccgccacg ggagcagcag cagcagcgtc gtcggcgccg     300
gcgaagcggc cgcgcggtgc ggcggcgggg cagcagcagt gcccgtcgtg cgcggtggac     360
gggtgcaagg aggacctgag caagtgccgc gactaccatc gccggcacaa ggtgtgcgag     420
gcccactcca gaccccct cgtcgtcgtc tccggccgcg agatgcgctt ctgccagcag     480
tgcagcaggt ttcacttgct tcaggagttt gatgaggcca agcgcagctg tagaaagcga    540
ctagatgggc acaaccgtcg ccgcaggaag ccacagccag atcccatgaa ctctgcaagt    600
tatcttgcaa gccaacaagg ggcaagattc tcaccgttcg cgacgccgag accggaggca    660
```

| | |
|---|---|
| agctggacag ggatgatcaa aaccgaggag agcccatact acacgcacca ccaaatccct | 720 |
| cttggcatca gcagcaggca gcagcatttc gttggctcca cctctgacgg cggccgccgc | 780 |
| ttcccttttcc tccaggaagg cgagatcagc ttcggcaccg gcgccggcgc cggcggcgtg | 840 |
| ccaatggatc aggcagcagc tgctgctgct gcttcagtgt gccagccact tctgaagacg | 900 |
| gtagctcctc ctcctcctcc tcatggcggc ggcggcagcg gcggcggcaa gatgttctcc | 960 |
| gatggtgggt tgacacaagt gctcgactcc gattgtgctc tctctctctt ctgtcagctc | 1020 |
| cggcgaactc cacggccatc gacgtcggcg gtggccgggt ggtcgtccag ccgaccgagc | 1080 |
| acatccccat tgcgcagcct ctcatctctg gccttcaatt cggcggcggc ggcggcagct | 1140 |
| cagcctggtt cgcggcgcgg ccgcatcatc aggcggccac cggcgccacc gccaccgccg | 1200 |
| tcgtcgtctc gacggccggt ttctcctgcc cggtggtgga gagcgagcag ctgaacacag | 1260 |
| tcctgagctc caatgacaat gagatgaact acaatgggat gtttcacgtc ggcggcgaag | 1320 |
| gctcatcgga tggcacgtcg tcgtctctgc cgttctcatg gcagtag | 1367 |

<210> SEQ ID NO 4
<211> LENGTH: 5068
<212> TYPE: DNA
<213> ORGANISM: Oryza sativa

<400> SEQUENCE: 4

| | |
|---|---|
| acagctcaag cttacgcggg agctaagctg agctgagctg agctacagcg agcggcggcg | 60 |
| gcggccatgg agtgggatct caagatgccg ccggcggcga gttgggagct agccgacgag | 120 |
| ctggagaaca gcggcggcgg gggtgtaccg gcggcggtat cgtcgtcatc ggctgcggtt | 180 |
| ggtggcggcg tcaatgcggg gggtggtggc aggcaggagt gctcggtcga cctcaagctc | 240 |
| ggcgggttgg gggagttcgg cggcggcggc gcgcagccgc gggtcgccgt ggcgggcgag | 300 |
| ctggccaagg ggaaggggcc agcggccgcc gccacgggag cagcagcagc agcgtcgtcg | 360 |
| gcgccggcga gcggccgcg cggtgcggcg cggggcagc agcagtgccc gtcgtgcgcg | 420 |
| gtggacgggt gcaaggagga cctgagcaag tgccgcgact accatcgccg gcacaaggtg | 480 |
| tgcgaggccc actccaagac cccctcgtc gtcgtctccg gccgcgagat gcgcttctgc | 540 |
| cagcagtgca gcaggtaacc cccccccccc ccccccaac cattgtctcc ttccttcccg | 600 |
| ccaaattcac tgcaaaacaa aaaaaaaatc gtagcccaaa acaccccaag acgtcatggc | 660 |
| aatcgcatca agaactgcat atatcaattt ctccacttct tttcagcgtc actgtctctg | 720 |
| atcattctct tgctgaaaca aaagaaaaag aagataagca agagttttttc tcttttttttt | 780 |
| gctccttttt tttttggctt tgcacaatct cttcttgctt ccagttgcaa ctgaccattg | 840 |
| tgcagtacat gcatctgcat ctactgattc taatttctac gctacttcgg atcaaaatta | 900 |
| attcagtact gcaaagcaca atttcattga tccatttcat ccagcctcgg actttgttca | 960 |
| tcatcatcta tctgtctctt acttccttc cattgggagc atactatccg gctgtctcgt | 1020 |
| ttcagggacg cacagctttg cctttaatgg catgccttttt cagccttccc tcatgctatc | 1080 |
| ctttagctcg gcaactcgta ttaccccaaa ttattgcctc tttgctcgcc tttagattta | 1140 |
| ttactatcat ctttttcttt cttttttata tctcttcttc accagtagct gcactgtttt | 1200 |
| tgcactgctc aagagcaaag cagctgctgt agttgttcag tgtttgttgc ttactgagaa | 1260 |
| aaaaaagtga tagagacaga aaaaaagtg agggagagaa aaaaaaaaa aacagaactg | 1320 |
| gcgcctgaat ctcatcagcc agagatcaca ttaggcaatt taccaccaga ctgttatgat | 1380 |
| attattttca gtgtcctcct gtctgaatat gagcgtctgc ttcctctaac aagaacaata | 1440 |

```
aatcagcacc tagttcagta ctaactaatt ttctcatgaa taaataaata aataaataaa    1500
tatagtcact gtaattagtg acactactag cacggtagca cctggtttag tggttaacaa    1560
tacttggttc ttgcacttct ccctgtcgat gttttttcgc gtgggggcta gctatcgatt    1620
gattgattcc tcaactatgg catcgaaact ggaagaacat atgcatactg gacacacac     1680 cctgcttgct ttctgaattt ctgatttctc ctcaaggcag ctggcctacc acatatatct    1740
gactgagctg tgctgcttct tgccatgaga gctaagctac cttagcttag ctactactac    1800
cacttactac gccgtctgtt ttggaaggga aaggcagatg tggatgccca aacctagaaa    1860
gatggttgta ccactgaaag agagagtttg tggatgtgat ctgcactaaa gcacccctgt    1920
acagggaaag gactatgtag ccctactaca agttcaccat ttacacctct gttcctaagg    1980
ttgggccaca catatatgaa gcttttaatg tctcggtttg ttggaaaggg ttttgcattg    2040
ccattacaag ccagcacagt ggatacagat agccagggtg ctctctattg gagaagaaaa    2100
aaaatggagc cctgaacacc ctgattggaa ctcactattg catgaaagaa tgatgagatt    2160
tcttgtctta tagttttaa agattttttt tctaaagtca gtcttagtta cattcatttg     2220
ttatattcca gtttcagact tattggcact aggttctgtg atctttttt ttttttaca      2280 tcgtttgagt atcatagggt gattcagtac caccttgacc cctgttttta tcagagctct    2340
aaacttctaa caccacttct aacttttgag ctagtcttct aaccttgctg ttttctgaac    2400
aaagatgtat actcaagatt ggtcatagat ggagatattc tgtgaacaga actaacataa    2460
tagcaccaaa ttagtcagac atactcttta caaaattact ttggagtttg ttgcccactc    2520
cttgaactag tacaatattg tcctactgat gccttcctgc ctttcaactt gaaagttccc    2580
tattttatct gttagttctt ttataaaatg taactgcaca ttgtcagaag gatttgcatc    2640
ttatttcact ttgcgccagt tttaagtaat acatggtata ttggcataag accagactct    2700
accatttttt atcttgcaga gacatagcaa acaactaagt acttttatt gtggtgtgct     2760 cctttacaca gtagcacaac ttgtaggatg cttatgtgat tgtctcatca attattctct    2820
ttatctttaa aaagagaatg atacaaaaaa tctctttatc tgagaataca cattacccag    2880
tggggacagt ctttcaatga tttgattact tcgtcagtgt ttgcaaactg gaagatcat     2940 tatgctgctg catgcagact ttataaatta agtgatcttc agagtcagaa caagatgtta    3000
gctttctata cctatggatc cacatccact gtattgtggt ccatgtacaa gtgggattaa    3060 aatattttc tgccgttgac agaacttcag ttcaataaat ttatctaaga tgaagtatcc     3120
aagcacggaa agagctaatt aactgatgaa ttcctgtggt cccttgtgta ggtatatgag    3180
tattctaaga gagaatatgg agacagtata ttaaattatt ctgagaatac ttatcctgac    3240
gtttctttag tgagaactgt ggtgcatcct tacaaaactt cagatcatgt tcaggagta    3300 ttttatcatg taagaatttt aaaaagacgt acatcctagg tacagtcatt tcttaaggtt    3360
tcatggtact gaatgattaa attacttctt ctggattggg tttcaagcat catttggcta    3420
atttcaatgc agttaaatga tcataggctt ttctttcttc aggtttcact tgcttcagga    3480
gtttgatgag gccaagcgca gctgtagaaa gcgactagta gggcacaacc gtcgccgcag    3540
gaagccacag ccagatccca tgaactctgc aagttatctt gcaagccaac aaggtatttt    3600
cttgttattt attaccactc tatgatatcg cagttcatat aagattaact gggatatagt    3660
cattcagact tcctaactat tgttagacta ggaaaaaaac tatgaaacat gctaatagca    3720
tagataagtc atggtaaaaa aaaagtaaa aaaaaatgaa actgtggtta aaaaaaacgc     3780
```

-continued

| | |
|---|---|
| aaatattagg gaatgaccta atatcaaata attagaagga gtgaggcttc aaacccaggt | 3840 |
| cgtctagccc atcatctttt gaagctagcc aaaaaacccc tgggcgtttc tcggaactgt | 3900 |
| ggttcagcta tgactctgtt ctttcaatcc tgacatcttg taacatgtaa tgcattctag | 3960 |
| tatacatcta atgcattgaa ccatatctta tgtactaatt tgtgctgata tcaaaacat | 4020 |
| cgcatcaaaa ttcaggggca agattctcac cgttcgcgac gccgagaccg gaggcaagct | 4080 |
| ggacagggat gatcaaaacc gaggagagcc catactacac gcaccaccaa atccctcttg | 4140 |
| gcatcagcag caggcagcag catttcgttg gctccacctc tgacggcggc cgccgcttcc | 4200 |
| ctttcctcca ggaaggcgag atcagcttcg gcaacggcgc cggcgccggc ggcgtgccaa | 4260 |
| tggatcaggc agcagctgct gctgctgctt cagtgtgcca gccacttctg aagacggtag | 4320 |
| ctcctcctcc tcctcctcat ggcggcggcg gcagcggcgg cggcaagatg ttctccgatg | 4380 |
| gtgggttgac acaagtgctc gactccgatt gtgctctctc tcttctgtca gctccggcga | 4440 |
| actccacggc catcgacgtc ggcggtggcc gggtggtcgt ccagccgacc gagcacatcc | 4500 |
| ccattgcgca gcctctcatc tctggccttc agttcggcgg cggcggcggc agctcagcct | 4560 |
| ggttcgcggc gcggccgcat catcaggcgg ccaccggcgc cgccgccacc gccgtcgtcg | 4620 |
| tctcgacggc cggtttctcc tgcccggtgg tggagagcga gcagctgaac acagtcctga | 4680 |
| gctccaatga caatgagatg aactacaatg ggatgtttca cgtcggcggc gaaggctcat | 4740 |
| cggatggcac gtcgtcgtct ctgccgttct catggcagta gttttttcag taactgtatg | 4800 |
| ttgctgcctt agtttcagta gagttggttc ttcatttctt ttcagtgatc aaattattgt | 4860 |
| ttctgttctt ttctgccatg gtaagttcct ttttttttct tcttcttctt gccttcattt | 4920 |
| gagttaatta cagcattgat ttgtgtgaac aaaattcatc ataaatcagt tcctcgcgag | 4980 |
| atcattggtc tcaacatgat ggtgccaagt gagaactgca gtattgtgca gttttcagtt | 5040 |
| ttgagtctaa gttgtataaa cttgcagt | 5068 |

```
<210> SEQ ID NO 5
<211> LENGTH: 5040
<212> TYPE: DNA
<213> ORGANISM: Oryza sativa

<400> SEQUENCE: 5
```

| | |
|---|---|
| acagctcaag cttacgcggg agctaagctg agctacagcg agcggcggcg gcggccatgg | 60 |
| agtgggatct caagatgccg ccggcggcga gctgggagct agccgacgag ctggagaaca | 120 |
| gcggcggcgg gggtgtaccg gcggcggtat cgtcgtcatc ggctgcggtt ggtggcggcg | 180 |
| tcaatgcggg gggtggtggc aggcaggagt gctcggtcga cctcaagctc ggcgggttgg | 240 |
| gggagttcgg cggcggcggc gcgcagccgc gggtcgccgt ggcgggcgag ccggccaagg | 300 |
| ggaagggcc agcggccgcc gccacgggag cagcagcagc agcgtcgtcg gcgccggcga | 360 |
| agcggccgcg cggtgcggcg gcggcgggc agcagcagtg cccgtcgtgc gcggtggacg | 420 |
| ggtgcaagga ggacctgagc aagtgccgcg actaccatcg ccggcacaag gtgtgcgagg | 480 |
| cccactccaa gacccccctc gtcgtcgtct ccggccgcga gatgcgcttc tgccagcagt | 540 |
| gcagcaggta accccccccc caaccattgt ctccttcctt cccgccaaat tcactgcaaa | 600 |
| acaaaaaaaa tcgtagccca aaacacccca agacgccgtg gcaattcgca tcaagaactg | 660 |
| catatatcaa tttctccact tctcttcagc gtcactgtct ctgatcattc tctttgctga | 720 |
| acaaaagaaa aagaagataa gcaagagttt ttctcttttt tttgctcctt ttttttggc | 780 |
| tttgcacaat ctcttcttgc ttccagttgc aactgaccat tgtgcagtac atgcatctgc | 840 |

```
atctactgat tctaatttct acgctacttc ggatcaaaat taattcagta ctgcaaagca    900
caatttcatt gatccatttc atccagcctc ggactttgtt catcatcatc tatctgtctc    960
ttacttcctt tccattggga gcatactatc cggctgtctc gtttcaggga cgcacagctt   1020
tgcctttaat ggcatgcctt ttcagccttc cctcatgcta tcctttagct cggcaactcg   1080
tattacccca aattattacc tctttgctcg cctttagatt tattactatc atcttttctt   1140 ttcttttta tatctcttct tcaccagtag ctgcactgtt tttgcactgc tcaagagcaa    1200
agcagctgct ggagttgttc agtgtttgtt gcttactgag aaaaaaaagt gatagagaca   1260
gaaaaaaaag tgagggagag aaaaaaaaaa aacagaactg acgcctgaat ctcatcagcc   1320
agagatcaca ttaggcaatt taccaccaga ctgttatgat attattttca gtgtcctcct   1380
gtctgaatat gaccgtctgc ttcctctaac aagaacaata aatcagcacc tagttcagta   1440
ctaactaatt ttctcatgaa taaataaata aatatagtca ctgtaattag tgacactact   1500
agcacggtag cacctggttt agtggttaac aatacttggt tcttgcactt ctccctgtcg   1560
atgttttttc gcgtggggc tagctatcga ttgattgatt cctcaactat ggcatcgaaa    1620
ctggaagaac atatgcatac tgggacacac accctgcttg cttctgaatt tctgatttc    1680 tcctcaaggc agctggccta ccacatatat ctgactgagc tgtgctgctt cttgccatga   1740
gagctaagct accttagctt agctactact accacttact acgccgtctg ttttggaagg   1800
gaaaggcaga tgtggatgcc caaacctaga aagatggttg taccactgaa agagagagtt   1860
tgtggatgtg atctgcacta aagcacccct gtacagggaa aggaccatgt agccctacta   1920
caagttcacc atttacacct ctgttcctaa ggttgggcca cacatatatg aagcttttaa   1980
tgtctcggtt tgttggaaag ggttttgcat tgccattaca agccagcaca gtggatacag   2040
atagccaggg tgctctctat tggagaagaa aaaaatgga gccctgaaca ccctgattgg    2100
atctcactat tgcatgaaag aatgatgaga tttcttgtct tataatttt aaagattttt    2160 tttctaaagt cagtcttagt tacattcatt tgttatattc cagtttcaga cttattggta   2220
ctaggttctg tgagatcttt ttttttttta catcgtttga gtatcatagg gtgattcagt   2280
accaccttga ccctgttttt tatcagagct ctaaacttct aacaccactt ctaacttttg   2340
agctagtctt ctaaccttgc tgttttctga acaaagatgt atactcaaga ttggtcatag   2400
atggagatat tctgtgaaca gaactaacat aatagcacca aattagtcag acatactctt   2460
tacaaaatta ctttggagtt tgttgtccac tccttgaact agtacaatat tgtcctactg   2520
aatgccttcc tgccttttcaa cttgaaagtt ccctattta tctgttagtt cttttataaa    2580
atgtaactgc acattgtcag aaggatttgc atcttatttc actttgcgcc agttttaagt   2640
aatacatggt atattggcat aagaccagac tctaccattt tttatcttgc agagacatag   2700
caaacaacta agtacttttt attgtggtgt gctcctttac acagtagcac aacttgtagg   2760
atgcttatgt gattgtctca tcaattattc tctttatctt taaaaagaga atgatacaaa   2820
aaatctcttt atctgagaat acacattacc cagtggggac agtctttcaa tgatttgatt   2880
acttcgtcag tgtttgcaaa ctgggaagat cattatgctg ctgcatgcag actttataaa   2940
ttaagtgatc ttcagagtca gaacaagatg ttagcttct ataccatgg atccacatcc    3000 actgtattgt ggtccatgta caagtggggt taaaatattt ttctgccgtt gacagaactt   3060
cagttcaata aatttatcta agatgaagta tccaagcacg gaaagagcta attaactgat   3120
gaaattcctg tggtcccttg tgttggtata tgagtattct aagagagaat atggagacag   3180
```

| | | | | |
|---|---|---|---|---|
| tatattaaat | tattctgaga | atacttatcc | tgacgtttct | ttagtgagaa ctgtggtgca | 3240 |
| tcgttacaaa | acttcagatc | atgtttcagg | agtattttat | catgtaagaa ttttaaaaag | 3300 |
| acgtacatcc | taggtacagt | catttcttaa | ggtttcatgg | tactgaatga ttaaattact | 3360 |
| tcttctggat | tgggtttcaa | gcatcatttg | gctaatttca | atgcagttaa atgatcataa | 3420 |
| gcttttcttt | cttcaggttt | cacttgcttc | aggagtttga | tgaggccaag cgcagctgta | 3480 |
| gaaagcgact | agatgggcac | aaccgtcgcc | gcaggaagcc | acagccagat cccatgaact | 3540 |
| ctgcaagtta | tcttgcaagc | caacaaggta | ttttcttgtt | tattattacc actctatgat | 3600 |
| atcgcagttc | atataagatt | aactgggata | tagtcattca | gacttcctaa ctattgttag | 3660 |
| actaggaaaa | aaactatgaa | acatgctaat | agcatagata | agtcatggta aaaaaaaagt | 3720 |
| aaaagaaaat | gaaactgtgg | ttaaaaaaaa | acgcaaatat | tagggaatga cctaatatca | 3780 |
| aataattaga | aggagtgagg | cttcgaaccc | aggtcgtcta | gcccatcacc ttttgaagct | 3840 |
| agccagaaaa | cccctgggcg | tttctcagaa | ctgtggttca | gctatgactc tgttctttca | 3900 |
| atcctgacat | cttgtaacat | gtaatgcatt | ctagtataca | tctaatgcat tgaaccatat | 3960 |
| cttatgtact | aatttgtgct | gatatatcaa | acatcgcatc | aaaattcagg ggcaagattc | 4020 |
| tcaccgttcg | cgacgccgag | accggaggca | agctggacag | gatgatcaa aaccgaggag | 4080 |
| agcccatact | acacgcacca | ccaaatccct | cttggcatca | gcagcaggca gcagcatttc | 4140 |
| gttggctcca | cctctgacgg | cggccgccgc | ttccctttcc | tccaggaagg cgagatcagc | 4200 |
| ttcggcaccg | gcgccggcgc | cggcggcgtg | ccaatggatc | aggcagcagc tgctgctgct | 4260 |
| gcttcagtgt | gccagccact | tctgaagacg | gtagctcctc | ctcctcctcc tcatggcggc | 4320 |
| ggcggcagcg | gcggcggcaa | gatgttctcc | gatggtgggt | tgacacaagt gctcgactcc | 4380 |
| gattgtgctc | tctctcttct | gtcagctccg | gcgaactcca | cggccatcga cgtcggcggt | 4440 |
| ggccgggtgg | tcgtccagcc | gaccgagcac | atccccatgg | cgcagcctct catctctggc | 4500 |
| cttcagttcg | gcggcggcgg | cggcagctca | gcctggttcg | cggcgcggcc gcatcatcag | 4560 |
| gcggccaccg | gcgccgccgc | caccgccgtc | gtcgtctcga | cggccggttt ctcctgcccg | 4620 |
| gtggtggaga | gcgagcagct | gaacacagtc | ctgagctcca | atgacaatga gatgaactac | 4680 |
| aatgggatgt | tcacgtcgg | cggcgaaggc | tcatcggatg | gcacgtcgtc gtctctgccg | 4740 |
| ttctcatggc | agtagttttt | tcagtaactg | tatgttgctg | ccttagtttc agtagagttg | 4800 |
| gttcttcatt | tcttttcagt | gatcaaatta | ttgtttctgt | tcttttctgc catggtaagt | 4860 |
| tccttttttt | tttcttcttc | ttgccttcat | ttgagttaat | tacagcattg atttgtgtga | 4920 |
| acaaaattca | tcataaatca | gttcctcgcg | agatcattgg | tctcaacatg atggtgccaa | 4980 |
| gtgagaactg | cagtattgtg | cagttttcag | ttttgagtct | aagttgtata aacttgcagt | 5040 |

<210> SEQ ID NO 6
<211> LENGTH: 5060
<212> TYPE: DNA
<213> ORGANISM: Oryza sativa

<400> SEQUENCE: 6

| | | | | |
|---|---|---|---|---|
| acagctcaag | cttacgcggg | agctaagctg | agctgagctg | agctacagcg agcggcggcg | 60 |
| gcggccatgg | agtgggatct | caagatgccg | ccggcggcga | gctgggagct agccgacgag | 120 |
| ctggagaaca | gcgcggcgg | gggtgtaccg | gcggcggtat | cgtcgtcatc ggctgcggtt | 180 |
| ggtggcggcg | tcaatgcggg | gggtggtggc | aggcaggagt | gctcggtcga cctcaagctc | 240 |
| ggcgggttgg | gggagttcgg | cggcggcggc | gcgcagccgc | gggtcgccgt ggcgggcgag | 300 |

```
ctggccaagg ggaaggggcc agcggccgcc gccacgggag cagcagcagc agcgtcgtcg      360
gcgccggcga agcggccgcg cggtgcggcg gcggggcagc agcagtgccc gtcgtgcgcg      420
gtggacgggt gcaaggagga cctgagcaag tgccgcgact accatcgccg gcacaaggtg      480
tgcgaggccc actccaagac cccctcgtc gtcgtctccg gccgcgagat gcgcttctgc       540
cagcagtgca gcaggtaacc cccccccccc ccaaccatgc tcttccttcc cgccaaattc      600
actgcaaaac aaaaaaaaaa tcgtagccca aacaccccca agacgtcatg caattcgca       660 tcaagaactg catatatcaa tttctccact tcttttcagc gtcactgtct ctgatcattc      720
tctttgctga acaaaagaaa aagaagataa gcaagagttt ttctcttttt tttgctcctt     780
tttttttttg gctttgcaca atctcttctt gcttccagtt gcaactgacc attgtgcagt      840
acatgcatct gcatctactg attctaattt ctacgctact tcggatcaaa attaattcag      900
tactgcaaag cacaatttca ttgatccatt tcatccagcc tcggactttg ttcatcatca     960
tctatctgtc tcttacttcc tttccattgg gagcatacta tccggctgtc tcgtttcagg      1020
gacgcacagc tttgccttta atggcatgcc ttttcagcct tccctcatgc tatcctttag      1080
ctcggcaact cgtattaccc caaattattg cctcttttgc tcgcctttag atttattact     1140
atcatctttt cttttctttt ttatatctct tcttcaccag tagctgcact gttttttgcac      1200 tgctcaagag caaagcagct gctgtagtta ttcagtgttt gttgcttact gagaaaaaaa      1260
agtgatagag acagaaaaaa aagtgaggga gagaaaaaaa aaaacagaa ctgacgcctg      1320 aatctcatca gccagagatc acattaggca atttaccacc agactgttat gatattattt      1380
tcagtgtcct cctgtctgaa tatgagcgtc tgcttcctct aacaagaaca ataaatcagc      1440
acctagttca gtactaacta attttctcat gaataaataa ataaataaat aaatatagtc      1500
actgtaatta gtgacactac tagcacggta gcacctggtt tagtggttaa caatacttgg      1560
ttcttgcact ctccctgtc gatgtttttt cgcgtggggg ctagctatcg attgattgat      1620
tcctcaacta tggcatcgaa actggaagaa catatgcata ctgggacaca caccctgctt      1680
gctttctgaa tttctgattt ctcctcaagg cagctggcct accacatata tctgactgag      1740
ctgtgctgct tcttgccatg agagctaagc taccttagct tagctactac taccacttac      1800
tacgccgtct gttttggaag ggaaaggcag atgtggatgc ccaaacctag aaagatggtt      1860
gtaccactga aagagagagt ttgtggatgt gatctgcact aaagcacccc tgtacaggga     1920
aaggactatg tagccctact acaagttcac catttacacc tctgttccta aggttgggcc     1980
acacatatat gaagctttta atgtctcggt tgttggaaa gggttttgca ttgccattac      2040
aagccagcac agtggataca gatagccagg gtgctctcta ttggagaaga aaaaaaatgg     2100
agccctgaac accctgattg gatctcacta ttgcatgaaa gaatgatgag atttcttgtc    2160
ttataatttt taaagatttt tttctaaag tcagtcttag ttacattcat ttgttatatt     2220
ccagtttcag acttattggc actaggttct gtgagatctt tttttttta catcgtttga      2280 gtatcatagg gtgattcagt accaccttga ccctgttttt tatcagagct ctaaacttct    2340
aacaccactt ctaactttg agctagtctt ctaaccttgc tgttttctga acaaagatgt      2400
atactcaaga ttggtcatag atggagatat tctgtgaaca gaactaacat aatagcacca    2460
aattagtcag acatactctt tacaaaatta ctttggagtt tgttgtccac tccttgaact    2520
agtacaatat tgtcctactg aatgccttcc tgcctttcaa cttgaaagtt ccctatttta    2580
tctgttagtt cttttataaa atgtaactgc acattgtcag aaggatttgc atcttatttc    2640
```

-continued

```
actttgcgcc agttttaagt aatacatggt atattggcat aagaccagac tctaccattt    2700
tttatcttgc agagacatag caaacaacta agtactttt attgtggtgt gctcctttac    2760
acagtagcac aacttgtagg atgcttatgt gattgtctca tcaattattc tctttatctt    2820
taaaaagaga atgatacaaa aaatctcttt atctgagaat acacattacc cagtggggac    2880
agtctttcaa tgatttgatt acttcgtcag tgtttgcaaa ctgggaagat cattatgctg    2940
ctgcatgcag actttataaa ttaagtgatc ttcagagtca gaacaagatg ttagcttttct    3000 atacctatgg atccacatcc actgtattgt ggtccatgta caagtggggt taaaatattt    3060
ttctgccgtt gacagaactt cagttcaata aatttatcta agatgaagta tccaagcacg    3120
gaaagagcta attaactgat gaaattcctg tggtcccttg tgttggtata tgagtattct    3180
aagagagaat atggagacag tatattaaat tattctgaga atacttatcc tgacgttttct    3240 ttagtgagaa ctgtggtgca tccttacaaa acttcagatc atgtttcagg agtatttat    3300 catgtaagaa ttttaaaaag acgtacatcc taggtacagt catttcttaa ggtttcatgg    3360
tactgaatga ttaaattact tcttctggat tgggtttcaa gcatcatttg gctaatttca    3420
atgcagttaa atgatcatag cttttctttt cttcaggttt cacttgcttc aggagtttga    3480
tgaggccaag cgcagctgta gaaagcgact agatgggcac aaccgtcgcc gcaggaagcc    3540
acagccagat cccatgaact ctgcaagtta tcttgcaagc caacaaggta ttttcttgtt    3600
tattattacc actctatgat atcgcagttc atataagatt aactgggata tagtcattca    3660
gacttcctaa ctattgttag actaggaaaa aaactatgaa acatgctaat agcatagata    3720
agtcatggta aaaaaaagt aaagaaaatg aaactgtggt taaaaaaaac gcaaatatta    3780
gggaatgacc taatatcaaa taattagaag gagtgaggct tcgaacccag attgtctagc    3840
ccatcatctt ttgaagctag ccaaaaaacc cctgggcatt tctcggaact gtggttcagc    3900
tatgactctg tgcttttcaat cctgacatct tgtaacatgt aatgcattct agtatacatc    3960
taatgcattg aaccatatct tatgtactaa tttgtgctga tatatcaaac atcatcaaaa    4020
ttcaggggca agattctcac cgttcgcgac gccgagaccg gaggcaagct ggacagggat    4080
gatcaaaacc gaggagagcc catactcacg gcaccaccaa atccctcttg gcatcagcag    4140
caggcagcag catttcgttg gctccacctc tgacggcggc cgccgcttcc ctttcctcca    4200
ggaaggcgag atcagcttcg gcaccggcgc cggcgccggc ggcgtgccaa tggatcaggc    4260
agcagctgct gctgctgctt cagtgtgcca gccacttctg aagacggtag ctcctcctcc    4320
tcctcctcat ggcggcggcg gcagcggcgg cggcaagatg ttctccgatg gtgggttgac    4380
acaagtgctc gactccgatt gtgctctctc tctcttctgt cagctccggc gaactccacg    4440
gccatcgacg tcggcggtgg ccgggtggtc gtccagccga ccgagcacat ccccattgcg    4500
cagcctctca tctctggcct tcaattcggc ggcggcggcg gcagctcagc ctggttcgcg    4560
gcgcggccgc atcatcaggc ggccaccggc gccaccgcca ccgccgtcgt cgtctcgacg    4620
gccggtttct cctgcccggt ggtggagagc gagcagctga acacagtcct gagctccaat    4680
gacaatgaga tgaactacaa tgggatgttt cacgtcggcg gcgaaggctc atcggatggc    4740
acgtcgtcgt ctctgccgtt ctcatggcag tagtttttc agtaactgta tgttgctgcc    4800
ttagtttcag tagagttgat tcttcatttc ttttcagtga tcaaattatt gtttctgttc    4860
ttttctgcca tggtaagttc cttttttttt cttcttcttc ttgccttcat ttgagttaat    4920
tacagcattg atttgtgtga acaaaattca tcataaatca gttcctcgcg agatcattgg    4980
tctcaacatg atggtgccaa gtgagaactg cagtattgtg cagttttcag ttttgagtct    5040
```
aagttgtata aacttgcagt                                                   5060

<210> SEQ ID NO 7
<211> LENGTH: 1886
<212> TYPE: DNA
<213> ORGANISM: Oryza sativa

<400> SEQUENCE: 7
cttaatttta gagttgattt taattataag agtcctatct caaattattt ttgtcattca         60
ttttctataa gaccaagctc aactaataac ttttggggtt agactagtca gtacatgtaa        120
ctcctagctt aatatcacgt ttatgtatat cctcccaact catagcttaa acaaagaaaa        180
actcgctagc tagactagga gcaagagtct tttctatatc ttttttgcgtc cttttcggat       240
aatgggtgca agtgcgattg tttctatatt ggacttaaaa aaataatggg tgcaagtgca        300
gaggcaagtt tggcaattaa gaaagttgag atttttaaaa tggagggagg cagaatgtgt        360
ggttcaggca tgaccaaact tggaaacaat ctgtcggctt tgatttgctt tagttgatgt        420
gtggattatt ttaagctttc tcaggcagaa aggtggttag gctgctgaag caacaacaac        480
aacaaccggt gtttggtgat aattaaacct gttctattca tacagcactc atcaacagta        540
ttataacgca ttcatcagaa gaagaaggga aaaaaatct gctactattc ctgagggaaa         600
aaatatacc ccacctgttt taaaataact gacattaata ctattctctt ttaaacttta         660
accacttatc ttttttccta atattacaaa cactacaaat gatatcatgt tattaaagcg        720
aggtaaaact tttattcact tatagtccaa caatttgaga gcaattaatg gtcaaaaatt        780
aaatgaaaaa tagaaattct cggttattaa gaaatgagag taaacaagta ctctctctat        840
cccgcgaaaa accaacttag tacctaatat tgatatattc tagtactatt agtctagaca        900
aatctagctg ccaacattcg gttctagatt gattttttt tggacggagg gagtataatt         960
gagaaaggt caaattaata atggaatgga tggtattgcc ttgagcttta aaaacacaac        1020
cttttcacctc aataattgta gcacaaagca ccacaagccc ccttccatg gcagtgcaaa       1080
aagatcaaag catgcatatg gtccctgcag ggccggcca accccccctt tcttcaccat       1140
ttactactac tgctcatcct tcaaaaatgc ctgccaggga ttgaatggtt gcaagggaag       1200
cagaaaccca gcaaataata gcactgcaca gtacatgaat actacatgta cacagttata       1260
cactactccc ctacaccatc cttcactaca gcccccagtt gtttcttgca agtactgagt       1320
aactgactac ccccagttcc tgccctcttg ggccttggta ttgttgctcc aagatctttg       1380
ccactactcc tactttcctt attccactag aaatcatata tacctttctc actctacata       1440
atcccctct ccttagagtc tagttatata gatagacaga tctctatcaa ctctgaaact        1500
aacctctaag gtaatctcgg aatcttcagc tctcgtaaac agaatagtta aagactcttg       1560
cgagaatctt ctaataaagt ctaagtagct acagaaacca gaaacaaacc agtagtaact       1620
taccaaccag atacgtaaca taacatgctg ctccctcagaa cctaaagcct ttttttttca     1680
ggggggtct aataatgatg tgattacgtc gcatctaact tgtgatggca attagtaagc        1740
agtagaggga gagggggaga gatgtgtttg tcctactaat aatgcgagtg gtgatctgat       1800
ctctgcttgc aaaagagaca gccacggaat cgagagtgag gaggccagcc aagaaaagcg       1860
acaccagtgt gtgcgtgcgt caacac                                           1886

<210> SEQ ID NO 8
<211> LENGTH: 1887
<212> TYPE: DNA

<213> ORGANISM: Oryza sativa

<400> SEQUENCE: 8

| | | | | | |
|---|---|---|---|---|---|
| cttaattttta | gagctgattt | taattataag | agtcctatct | caaattattt | ttgtcattca | 60 |
| ttttctataa | gaccaagctc | aactaataac | ttttggggtt | agactagtca | gtacatgtaa | 120 |
| ctcctagctt | aatatcacgt | ttatgtatat | cctcccaact | catagcttaa | acaaagaaaa | 180 |
| actcgctagc | tagactagga | gcaagagtct | tttctatatc | tttttgcgtc | cttttcggat | 240 |
| aatgggtgca | agtgcgattg | tttctatatt | ggacttaaaa | aaataatggg | tgcaagtgca | 300 |
| gaggcaagtt | tggcaattaa | gaaagttgag | attttaaaa | tggagggagg | cagaatgtgt | 360 |
| ggttcaggca | tgaccaaact | tggaaacaat | ctgtcggctt | tgatttgctt | tagttgatgt | 420 |
| gtggattatt | ttaagctttc | tcaggcagaa | aggtggttag | gctgctgaag | caacaacaac | 480 |
| aacaaccggt | gtttggtgat | aattaaacct | gttctattca | tacagcactc | aacaacagta | 540 |
| ttataacgca | ttcatcagaa | gaagaaggga | aaaaaatct | gctactattc | ctgagggaaa | 600 |
| aaaaatatac | cccacctgtt | ttaaaataac | tgacattgat | actattctct | tttaaacttt | 660 |
| aaccacttat | cttttttcct | aatattacaa | acactacaaa | tgatatcatg | ttattaaagc | 720 |
| gaggtaaaac | ttttattcac | ttatagtcca | acaatttgag | agcaattaat | ggtcaaaaat | 780 |
| taaatgaaaa | atagaaattc | ttggttatta | agaaatgaga | gtaaacaagt | actctctcta | 840 |
| tcccgcgaaa | aaccaactta | gtacctaatg | ttcatatatt | ctagtactat | gagtctagac | 900 |
| aaatctagct | gccaacattc | ggttctagat | tgattttttt | ttggacggag | ggagtataat | 960 |
| tgagaaaagg | tcaaattaat | aatggaatgg | atggtattgc | cttgagcttt | aaaaacacaa | 1020 |
| cctttcacct | caataattgt | agcacaaagc | accacaagcc | cccttccat | ggcagtgcaa | 1080 |
| aaagatcaaa | gcatgcatat | ggtccctgca | gggcccggcc | aaccccccct | ttcttcacca | 1140 |
| tttactacta | ctgctcatcc | ttcaaaaatg | cctgccaggg | attgaatggt | tgcaagggaa | 1200 |
| gcagaaaccc | agcaaataat | agcactgcac | agtacatgaa | tactacatgt | acacagttac | 1260 |
| acactactcc | cctacaccat | ccttcactac | agccccagt | tgtttcttgc | aagtactgag | 1320 |
| taactgacta | cccccagttc | ctgccctctt | gggccttggt | attgttgctc | caagatcttt | 1380 |
| gccactactc | ctactttcct | tattccacta | gaaatcatat | ataccttct | cactctacat | 1440 |
| aatccccctc | tccttagagt | ctagttatat | agatagacag | atctctatca | actctgaaac | 1500 |
| taacctctaa | ggtaatctcg | gaatcttcag | ctctcgtaaa | cagaatagtt | aaagactctt | 1560 |
| gcgagaatct | tctaataaag | tctaagtagc | tacagaatcc | agaaacaaac | cagtagtaac | 1620 |
| ttaccaacca | gatacgtaac | ataacatgct | gctccttaga | acctaaagcc | ttttttttc | 1680 |
| aaggggggtg | taataatgat | gtgattacgt | cgcatctaac | ttgtgatggc | aattagtaag | 1740 |
| cagtagaggg | agaggggag | agatgtgttt | gtcctactaa | taatgcgagt | ggtgatctga | 1800 |
| tctctgcttg | caaagagac | agccacggaa | tcgagagtga | ggaggccagc | caagaaaagc | 1860 |
| gacaccagtg | tgtgcgtgcg | tcaacac | | | | 1887 |

<210> SEQ ID NO 9
<211> LENGTH: 454
<212> TYPE: PRT
<213> ORGANISM: Oryza sativa

<400> SEQUENCE: 9

Met Glu Trp Asp Leu Lys Met Pro Pro Ala Ala Ser Trp Glu Leu Ala
1               5                   10                  15

```
Asp Glu Leu Glu Asn Ser Gly Gly Gly Val Pro Ala Ala Val Ser
            20                  25                  30
Ser Ser Ser Ala Ala Val Gly Gly Val Asn Ala Gly Gly Gly
        35                  40                  45
Arg Gln Glu Cys Ser Val Asp Leu Lys Leu Gly Gly Leu Gly Glu Phe
    50                  55                  60
Gly Gly Gly Gly Ala Gln Pro Arg Val Ala Val Ala Gly Glu Leu Ala
65                  70                  75                  80
Lys Gly Lys Gly Pro Ala Ala Ala Thr Gly Ala Ala Ala Ala
                85                  90                  95
Ser Ser Ala Pro Ala Lys Arg Pro Arg Gly Ala Ala Gly Gln Gln
            100                 105                 110
Gln Cys Pro Ser Cys Ala Val Asp Gly Cys Lys Glu Asp Leu Ser Lys
        115                 120                 125
Cys Arg Asp Tyr His Arg Arg His Lys Val Cys Glu Ala His Ser Lys
    130                 135                 140
Thr Pro Leu Val Val Ser Gly Arg Glu Met Arg Phe Cys Gln Gln
145                 150                 155                 160
Cys Ser Arg Phe His Leu Leu Gln Glu Phe Asp Glu Ala Lys Arg Ser
                165                 170                 175
Cys Arg Lys Arg Leu Asp Gly His Asn Arg Arg Arg Lys Pro Gln
            180                 185                 190
Pro Asp Pro Met Asn Ser Ala Ser Tyr Leu Ala Ser Gln Gln Gly Ala
        195                 200                 205
Arg Phe Ser Pro Phe Ala Thr Pro Arg Pro Glu Ala Ser Trp Thr Gly
    210                 215                 220
Met Ile Lys Thr Glu Glu Ser Pro Tyr Tyr Thr His His Gln Ile Pro
225                 230                 235                 240
Leu Gly Ile Ser Ser Arg Gln Gln His Phe Val Gly Ser Thr Ser Asp
                245                 250                 255
Gly Gly Arg Arg Phe Pro Phe Leu Gln Glu Gly Glu Ile Ser Phe Gly
            260                 265                 270
Asn Gly Ala Gly Ala Gly Gly Val Pro Met Asp Gln Ala Ala Ala Ala
        275                 280                 285
Ala Ala Ala Ser Val Cys Gln Pro Leu Leu Lys Thr Val Ala Pro Pro
    290                 295                 300
Pro Pro Pro His Gly Gly Gly Ser Gly Gly Gly Lys Met Phe Ser
305                 310                 315                 320
Asp Gly Gly Leu Thr Gln Val Leu Asp Ser Asp Cys Ala Leu Ser Leu
                325                 330                 335
Leu Ser Ala Pro Ala Asn Ser Thr Ala Ile Asp Val Gly Gly Gly Arg
            340                 345                 350
Val Val Val Gln Pro Thr Glu His Ile Pro Ile Ala Gln Pro Leu Ile
        355                 360                 365
Ser Gly Leu Gln Phe Gly Gly Gly Ser Ser Ala Trp Phe Ala
    370                 375                 380
Ala Arg Pro His His Gln Ala Ala Thr Gly Ala Ala Ala Thr Ala Val
385                 390                 395                 400
Val Val Ser Thr Ala Gly Phe Ser Cys Pro Val Val Glu Ser Glu Gln
                405                 410                 415
Leu Asn Thr Val Leu Ser Ser Asn Asp Asn Glu Met Asn Tyr Asn Gly
            420                 425                 430
Met Phe His Val Gly Gly Glu Gly Ser Ser Asp Gly Thr Ser Ser Ser
```

```
                           435                 440                 445

Leu Pro Phe Ser Trp Gln
            450

<210> SEQ ID NO 10
<211> LENGTH: 455
<212> TYPE: PRT
<213> ORGANISM: Oryza sativa

<400> SEQUENCE: 10

Met Glu Trp Asp Leu Lys Met Pro Ala Ala Ser Trp Glu Leu Ala
1               5                   10                  15

Asp Glu Leu Glu Asn Ser Gly Gly Gly Val Pro Ala Ala Val Ser
                20                  25                  30

Ser Ser Ser Ala Ala Val Gly Gly Val Asn Ala Gly Gly Gly Gly
            35                  40                  45

Arg Gln Glu Cys Ser Val Asp Leu Lys Leu Gly Gly Leu Gly Phe
        50                  55                  60

Gly Gly Gly Gly Ala Gln Pro Arg Val Ala Val Ala Gly Glu Pro Ala
65                  70                  75                  80

Lys Gly Lys Gly Pro Ala Ala Ala Thr Gly Ala Ala Ala Ala
                85                  90                  95

Ser Ser Ala Pro Ala Lys Arg Pro Arg Gly Ala Ala Ala Gly Gln
            100                 105                 110

Gln Gln Cys Pro Ser Cys Ala Val Asp Gly Cys Lys Glu Asp Leu Ser
        115                 120                 125

Lys Cys Arg Asp Tyr His Arg His Lys Val Cys Glu Ala His Ser
130                 135                 140

Lys Thr Pro Leu Val Val Ser Gly Arg Glu Met Arg Phe Cys Gln
145                 150                 155                 160

Gln Cys Ser Arg Phe His Leu Leu Gln Glu Phe Asp Glu Ala Lys Arg
                165                 170                 175

Ser Cys Arg Lys Arg Leu Asp Gly His Asn Arg Arg Arg Lys Pro
            180                 185                 190

Gln Pro Asp Pro Met Asn Ser Ala Ser Tyr Leu Ala Ser Gln Gln Gly
        195                 200                 205

Ala Arg Phe Ser Pro Phe Ala Thr Pro Arg Pro Glu Ala Ser Trp Thr
210                 215                 220

Gly Met Ile Lys Thr Glu Glu Ser Pro Tyr Tyr Thr His His Gln Ile
225                 230                 235                 240

Pro Leu Gly Ile Ser Ser Arg Gln Gln His Phe Val Gly Ser Thr Ser
                245                 250                 255

Asp Gly Gly Arg Arg Phe Pro Phe Leu Gln Glu Gly Glu Ile Ser Phe
            260                 265                 270

Gly Thr Gly Ala Gly Ala Gly Gly Val Pro Met Asp Gln Ala Ala Ala
        275                 280                 285

Ala Ala Ala Ser Val Cys Gln Pro Leu Leu Lys Thr Val Ala Pro
    290                 295                 300

Pro Pro Pro Pro His Gly Gly Gly Ser Gly Gly Gly Lys Met Phe
305                 310                 315                 320

Ser Asp Gly Gly Leu Thr Gln Val Leu Asp Ser Asp Cys Ala Leu Ser
                325                 330                 335

Leu Leu Ser Ala Pro Ala Asn Ser Thr Ala Ile Asp Val Gly Gly Gly
            340                 345                 350
```

```
Arg Val Val Val Gln Pro Thr Glu His Ile Pro Met Ala Gln Pro Leu
            355                 360                 365

Ile Ser Gly Leu Gln Phe Gly Gly Gly Gly Ser Ser Ala Trp Phe
370                 375                 380

Ala Ala Arg Pro His His Gln Ala Ala Thr Gly Ala Ala Thr Ala
385                 390                 395                 400

Val Val Val Ser Thr Ala Gly Phe Ser Cys Pro Val Val Glu Ser Glu
                405                 410                 415

Gln Leu Asn Thr Val Leu Ser Ser Asp Asn Glu Met Asn Tyr Asn
            420                 425                 430

Gly Met Phe His Val Gly Gly Glu Gly Ser Ser Asp Gly Thr Ser Ser
            435                 440                 445

Ser Leu Pro Phe Ser Trp Gln
    450                 455

<210> SEQ ID NO 11
<211> LENGTH: 417
<212> TYPE: PRT
<213> ORGANISM: Oryza sativa

<400> SEQUENCE: 11

Met Glu Trp Asp Leu Lys Met Pro Pro Ala Ala Ser Trp Glu Leu Ala
1               5                   10                  15

Asp Glu Leu Glu Asn Ser Gly Gly Gly Gly Val Pro Ala Ala Val Ser
            20                  25                  30

Ser Ser Ser Ala Ala Val Gly Gly Gly Val Asn Ala Gly Gly Gly Gly
        35                  40                  45

Arg Gln Glu Cys Ser Val Asp Leu Lys Leu Gly Gly Leu Gly Glu Phe
50                  55                  60

Gly Gly Gly Gly Ala Gln Pro Arg Val Ala Val Ala Gly Glu Leu Ala
65                  70                  75                  80

Lys Gly Lys Gly Pro Ala Ala Ala Ala Thr Gly Ala Ala Ala Ala Ala
                85                  90                  95

Ser Ser Ala Pro Ala Lys Arg Pro Arg Gly Ala Ala Ala Gly Gln Gln
            100                 105                 110

Gln Cys Pro Ser Cys Ala Val Asp Gly Cys Lys Glu Asp Leu Ser Lys
        115                 120                 125

Cys Arg Asp Tyr His Arg Arg His Lys Val Cys Glu Ala His Ser Lys
130                 135                 140

Thr Pro Leu Val Val Ser Gly Arg Glu Met Arg Phe Cys Gln Gln Cys
145                 150                 155                 160

Cys Ser Arg Phe His Leu Leu Gln Glu Phe Asp Glu Ala Lys Arg Ser
                165                 170                 175

Cys Arg Lys Arg Leu Asp Gly His Asn Arg Arg Arg Lys Pro Gln
            180                 185                 190

Pro Asp Pro Met Asn Ser Ala Ser Tyr Leu Ala Ser Gln Gln Gly Ala
        195                 200                 205

Arg Phe Ser Pro Phe Ala Thr Pro Arg Pro Glu Ala Ser Trp Thr Gly
210                 215                 220

Met Ile Lys Thr Glu Glu Ser Pro Tyr Tyr Thr His Gln Ile Pro
225                 230                 235                 240

Leu Gly Ile Ser Ser Arg Gln Gln His Phe Val Gly Ser Thr Ser Asp
                245                 250                 255

Gly Gly Arg Arg Phe Pro Phe Leu Gln Glu Gly Glu Ile Ser Phe Gly
            260                 265                 270
```

```
Thr Gly Ala Gly Ala Gly Gly Val Pro Met Asp Gln Ala Ala Ala
        275                 280                 285

Ala Ala Ala Ser Val Cys Gln Pro Leu Leu Lys Thr Val Ala Pro Pro
    290                 295                 300

Pro Pro Pro His Gly Gly Gly Ser Gly Gly Gly Lys Met Phe Ser
305                 310                 315                 320

Asp Gly Gly Leu Thr Gln Val Leu Asp Ser Asp Cys Ala Leu Ser Leu
                325                 330                 335

Phe Cys Gln Leu Arg Arg Thr Pro Arg Pro Ser Thr Ser Ala Val Ala
                340                 345                 350

Gly Trp Ser Ser Ser Arg Pro Ser Thr Ser Pro Leu Arg Ser Leu Ser
        355                 360                 365

Ser Leu Ala Phe Asn Ser Ala Ala Ala Ala Ala Gln Pro Gly Ser
    370                 375                 380

Arg Arg Gly Arg Ile Ile Arg Arg Pro Pro Ala Pro Pro Pro Pro
385                 390                 395                 400

Ser Ser Ser Arg Arg Pro Val Ser Pro Ala Arg Trp Trp Arg Ala Ser
                405                 410                 415

Ser

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 12
tcactgattc cctttacgt tt                                              22

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 13
gctcagttgc ttcttcatta ga                                             22

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 14
gccagccaag aaaagcgaca                                                20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 15
tcttgagatc ccactccatg                                                20
```

```
<210> SEQ ID NO 16
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 16
atgaccgtct gcttcctcta a                                              21

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 17
aacatcgaca gggagaagtg c                                              21

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 18
ttcagattgg gtatgctcat                                                20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 19
cattcagact ttcagaggca                                                20

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 20
gccatagtta tcgtcgttt                                                 19

<210> SEQ ID NO 21
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 21
ggagtatttg tttgtttcg                                                 19

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide primer
```

<400> SEQUENCE: 22
gagacgatgt gactgaaaag                                                20

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 23
atgaatctga acaaaggtat g                                              21

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 24
aaaggcgagt cgtggtaaag a                                              21

<210> SEQ ID NO 25
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 25
gatggagatg gtgagtgggt g                                              21

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 26
catcgcttcc aatgccctcc                                                20

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 27
ccctcttctc cgttctgacg                                                20

<210> SEQ ID NO 28
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 28
ctcagatgga actgaaggc                                                 19

<210> SEQ ID NO 29
<211> LENGTH: 20

-continued

```
<212> TYPE: DNA
<213> ORGANISM: Artificial Sequence
<220> FEATURE:
<223> OTHER INFORMATION: Oligonucleotide primer

<400> SEQUENCE: 29
caactggcta atatggtgct                                              20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 30
cccttgtgct gtctcctctc                                              20

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 31
acgggcttct tctccttctc                                              20

<210> SEQ ID NO 32
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 32
gcgatcgatg gctacgac                                                18

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 33
acaacccaac aagaaggacg                                              20

<210> SEQ ID NO 34
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 34
ttgaaggcgc tgaaggag                                                18

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 35
```

```
catcaacctc gtcttcaccg                                              20

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 36
accaagcatc cagtgaccag                                              20

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 37
gttcttcata cagtccacat g                                            21

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 38
gacaaaacac aaagcaggac                                              20

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 39
taacaaacca accaaccaag                                              20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 40
tcgtaggtgg ggctaacaag                                              20

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 41
caccctcttc ttcctccgac                                              20

<210> SEQ ID NO 42
<211> LENGTH: 21
<212> TYPE: DNA
<213> ORGANISM: Artificial Sequence
```

```
<220> FEATURE:
<223> OTHER INFORMATION: Oligonucleotide primer

<400> SEQUENCE: 42
aactcatttg tcacacgcac a                                              21

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 43
aagcctttcc tcgtaacacg                                                20

<210> SEQ ID NO 44
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 44
cgggatccca ggagtttgat gaggccaag                                      29

<210> SEQ ID NO 45
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 45
gctctagaaa gctgatctcg ccttcctgg                                      29

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 46
aagatgttct ccgatggtgg                                                20

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 47
atgtgctcgg tcggctggac                                                20
```

SPL16 COMPOSITIONS AND METHODS TO INCREASE AGRONOMIC PERFORMANCE OF PLANTS

CROSS REFERENCE

This utility application is a national stage application under 35 U.S.C §371 of PCT Application Number PCT/CN2012/081597 filed Sep. 19, 2012, which claims priority to Chinese Application No. CN201110294864.5, filed Sep. 30, 2011, both of which are incorporated herein by reference.

FIELD

The disclosure relates generally to the field of molecular biology.

BACKGROUND

The domestication of many plants has correlated with dramatic increases in yield. Most phenotypic variation occurring in natural populations is continuous and is effected by multiple gene influences. The identification of specific genes responsible for the dramatic differences in yield, in domesticated plants, has become an important focus of agricultural research.

Rice is a major dietary component for over half of the world's population. Simultaneous improvement of yield and end-use quality of rice remains a challenge. Grain size is a prime breeding target, as it affects both yield and quality. Genetic control of this trait has been extensively investigated over the last decade. However, many of the genetic determinants for grain size are currently explained only by quantitative trait loci (QTLs), without a detailed understanding of the nature of the encoded gene product. The present disclosure provides methods and compositions to improve grain size, shape and quality.

SUMMARY

The present disclosure provides polynucleotides, related polypeptides and all conservatively modified variants of a novel gene, OsSPL16 that has been shown to affect grain shape and quality in rice.

A method of improving grain width, weight or yield of a plant includes the steps of modulating the expression of (i) a polynucleotide encoding an amino acid sequence comprising one of SEQ ID NOS: 9-11 or an amino acid sequence that is at least 95% identical to one of SEQ ID NOS: 9-11 (ii) a polynucleotide that hybridizes under stringent hybridization conditions to a fragment of polynucleotide selected from the group consisting of SEQ ID NOS: 1-6, wherein the fragment comprises at least 100 contiguous nucleotides of SEQ ID NOS: 1-6 (iii) a polynucleotide that encodes an amino acid sequence that is at least 90% identical to SEQ ID NO: 9, (iv) a polynucleotide encoding a polypeptide comprising one or more deletions or insertions or substitution of amino acids compared to SEQ ID NO: 9, wherein the polynucleotide encodes a polypeptide involved in the regulation of grain width, weight or yield.

In an embodiment, the polynucleotide that comprises a fragment of SEQ ID NO: 1, is sufficient to down-regulate the endogenous expression of the polynucleotide that encodes a polypeptide involved in the regulation of rice grain width, weight or yield. In an embodiment, the modulation of the expression is achieved through RNA interference. In an embodiment, the modulation of the expression is achieved through mutagenesis. In an embodiment, the modulation of the expression is achieved through microRNA mediated gene silencing. In an embodiment, the modulation of the expression is achieved through promoter-mediated gene suppression. In an embodiment, the modulation of the expression is achieved through targeted mutagenesis of an endogenous regulatory element.

In an embodiment, the grain width is reduced in relation to a control plant not expressing the polynucleotide. In an embodiment, the grain weight is increased in relation to a control plant not expressing the polynucleotide.

In an embodiment, the modulation of expression is performed in a monocot. In an embodiment, the plant is rice. In an embodiment, the plant is a dicot.

A method of improving the length to width aspect of rice grain includes the steps of modulating the expression of a polynucleotide that encodes a polypeptide comprising the amino acid sequence of SEQ ID NO: 9 or an allelic variant thereof.

A method of improving rice grain yield, the method includes modulating the expression of a polynucleotide that encodes a polypeptide comprising the amino acid sequence of SEQ ID NO: 9 or a variant thereof.

A method of marker assisted selection of a plant for improved grain quality or yield, the method includes the steps of: performing marker-assisted selection of plants that have one or more variations in genomic regions encoding a protein comprising SEQ ID NO: 9 or a variant thereof or a regulatory sequence thereof; and identifying the plant that produces grains with improved grain quality and/or higher yield.

A method of identifying alleles in rice plants or rice germplasm that are associated with improved grain quality and/or increased yield, the method includes the steps of obtaining a population of rice plants, wherein one or more plants exhibit improved grain quality and/or increased yield; evaluating allelic variations with respect to the polynucleotide sequence encoding a protein comprising a polypeptide comprising: SEQ ID NO: 9 or in the genomic region that regulates the expression of the polynucleotide encoding the protein; obtaining phenotypic values of improved grain quality and/or increased yield for a plurality of rice plants in the population; associating the allelic variations in the genomic region associated with the polynucleotide with the phenotype; and identifying the alleles that are associated with improved grain quality and/or increased yield.

An isolated polynucleotide (i) encoding an amino acid sequence comprising one of SEQ ID NOS: 9-11 or an amino acid sequence that is at least 95% identical to one of SEQ ID NOS: 9-11 (ii) hybridizing under stringent hybridization conditions to a fragment of polynucleotide selected from the group consisting of SEQ ID NOS: 1-6, wherein the fragment comprises at least 100 contiguous nucleotides of SEQ ID NOS: 1-6 (iii) that encodes an amino acid sequence that is at least 90% identical to SEQ ID NO: 9, (iv) a polynucleotide encoding a polypeptide comprising one or more deletions or insertions or substitution of amino acids compared to SEQ ID NO: 9, wherein the polynucleotide encodes a polypeptide involved in the regulation of grain width, weight or yield.

A recombinant expression cassette, comprising the polynucleotide of claim 17, wherein the polynucleotide is operably linked, in sense or anti-sense orientation to a promoter, wherein the anti-sense recombinant construct produces a hairpin nucleotide molecule in a plant cell.

In an embodiment, a host cell includes the recombinant polynucleotides disclosed herein. In an embodiment, a transgenic plant includes the recombinant expression cassette disclosed herein.

An isolated polynucleotide that operably regulates the expression of a polynucleotide that encodes a polypeptide comprising the amino acid sequence of SEQ ID NO: 9 or a variant thereof. In an embodiment, the polynucleotide that regulates the expression comprises a sequence selected from the group consisting of SEQ ID NOS: 7-8 or a functional promoter fragment thereof.

A promoter inverted repeat construct comprising at least 100 contiguous nucleotides of the polynucleotides disclosed herein that function as regulatory elements.

TABLE 1

Sequence Identity

| SEQ ID NO: | Polynucleotide/ polypeptide | Identity | Description |
| --- | --- | --- | --- |
| SEQ ID NO: 1 | polynucleotide | OsSPL16-GW8 cDNA (wild-type) | Hua-jing-xian (HJX)74 |
| SEQ ID NO: 2 | polynucleotide | OsSPL16-GW8 cDNA (mutant 1) | W09-38-60-07-07-03-04-0049-16 |
| SEQ ID NO: 3 | polynucleotide | OsSPL16-GW8 cDNA (mutant 2) | W02-15-01-08-14-05-01-32 |
| SEQ ID NO: 4 | polynucleotide | OsSPL16-GW8 gDNA (wild-type) | HJX74 |
| SEQ ID NO: 5 | polynucleotide | OsSPL16-GW8 gDNA (mutant 1) | W09-38-60-07-07-03-04-0049-16 |
| SEQ ID NO: 6 | polynucleotide | OsSPL16-GW8 gDNA (mutant 2) | W02-15-01-08-14-05-01-32 |
| SEQ ID NO: 7 | polynucleotide | OsSPL16-GW8 promoter (wild-type) | HJX74 |
| SEQ ID NO: 8 | polynucleotide | OsSPL16-GW8 promoter (mutant) | W09-38-60-07-07-03-04-0049-16 |
| SEQ ID NO: 9 | polypeptide | OsSPL16-GW8 protein (wild-type) | HJX74 |
| SEQ ID NO: 10 | polypeptide | OsSPL16-GW8 protein (mutant 1) | W09-38-60-07-07-03-04-0049-16 |
| SEQ ID NO: 11 | polypeptide | OsSPL16-GW8 protein (mutant 2) | W02-15-01-08-14-05-01-32 |
| SEQ ID NO: 12 | primer | PSM709F | Cloning and mapping |
| SEQ ID NO: 13 | primer | PSM709R | Cloning and mapping |
| SEQ ID NO: 14 | primer | PSM710F | Cloning and mapping |
| SEQ ID NO: 15 | primer | PSM710R | Cloning and mapping |
| SEQ ID NO: 16 | primer | PSM711F | Cloning and mapping |
| SEQ ID NO: 17 | primer | PSM711R | Cloning and mapping |
| SEQ ID NO: 18 | primer | PSM712F | Cloning and mapping |
| SEQ ID NO: 19 | primer | PSM712R | Cloning and mapping |
| SEQ ID NO: 20 | primer | PSM733F | Cloning and mapping |
| SEQ ID NO: 21 | primer | PSM733R | Cloning and mapping |
| SEQ ID NO: 22 | primer | PSM734F | Cloning and mapping |
| SEQ ID NO: 23 | primer | PSM734R | Cloning and mapping |
| SEQ ID NO: 24 | primer | PSM736F | Cloning and mapping |
| SEQ ID NO: 25 | primer | PSM736R | Cloning and mapping |
| SEQ ID NO: 26 | primer | PSM695F | Cloning and mapping |
| SEQ ID NO: 27 | primer | PSM695R | Cloning and mapping |
| SEQ ID NO: 28 | primer | PSM699F | Cloning and mapping |
| SEQ ID NO: 29 | primer | PSM699R | Cloning and mapping |
| SEQ ID NO: 30 | primer | RM447F | Cloning and mapping |
| SEQ ID NO: 31 | primer | RM447R | Cloning and mapping |
| SEQ ID NO: 32 | primer | RM502F | Cloning and mapping |
| SEQ ID NO: 33 | primer | RM502R | Cloning and mapping |
| SEQ ID NO: 34 | primer | RM80F | Cloning and mapping |
| SEQ ID NO: 35 | primer | RM80R | Cloning and mapping |
| SEQ ID NO: 36 | primer | RM281F | Cloning and mapping |
| SEQ ID NO: 37 | primer | RM281R | Cloning and mapping |
| SEQ ID NO: 38 | primer | RM5493F | Cloning and mapping |
| SEQ ID NO: 39 | primer | RM5493R | Cloning and mapping |
| SEQ ID NO: 40 | primer | RM3754F | Cloning and mapping |
| SEQ ID NO: 41 | primer | RM3754R | Cloning and mapping |
| SEQ ID NO: 42 | primer | OSR7F | Cloning and mapping |
| SEQ ID NO: 43 | primer | OSR7R | Cloning and mapping |
| SEQ ID NO: 44 | Primer | RNAi-BamH IF | RNAi primer |
| SEQ ID NO: 45 | Primer | RNAi-XbaIR | RNAi primer |
| SEQ ID NO: 46 | Primer | GW8 internal F | GW8 internal PCR primer |
| SEQ ID NO: 47 | Primer | GW8 internal R | GW8 internal PCR primer |

REFERENCE TO SEQUENCE LISTING SUBMITTED ELECTRONICALLY

The official copy of the sequence listing is submitted electronically via EFS-Web as an ASCII formatted sequence listing with a file named "RTS16139BUSPCT_SeqList.txt" created on Mar. 27, 2014, and having a size of 52 kilobytes and is filed concurrently with the specification. The sequence listing contained in this ASCII formatted document is part of the specification and is herein incorporated by reference in its entirety.

In another aspect, the present disclosure relates to a recombinant expression cassette comprising a nucleic acid as described. Additionally, the present disclosure relates to a vector containing the recombinant expression cassette. Further, the vector containing the recombinant expression cassette can facilitate the transcription and translation of the nucleic acid in a host cell. The present disclosure also relates to the host cells able to express the polynucleotide of the present disclosure. A number of host cells could be used, such as but not limited to, microbial, mammalian, plant or insect.

In yet another embodiment, the present disclosure is directed to a transgenic plant or plant cells, containing the nucleic acids of the present disclosure. Preferred plants containing the polynucleotides of the present disclosure include but are not limited to maize, soybean, sunflower, sorghum, canola, wheat, alfalfa, cotton, rice, barley, tomato and millet. In another embodiment, the transgenic plant is a maize plant or plant cells. Another embodiment is the transgenic seeds from the transgenic nitrate uptake-associated polypeptide of the disclosure operably linked to a promoter that drives expression in the plant. The plants of the disclosure can have improved grain quality as compared to a control plant.

DETAILED DESCRIPTION OF THE FIGURES

Figure 3:
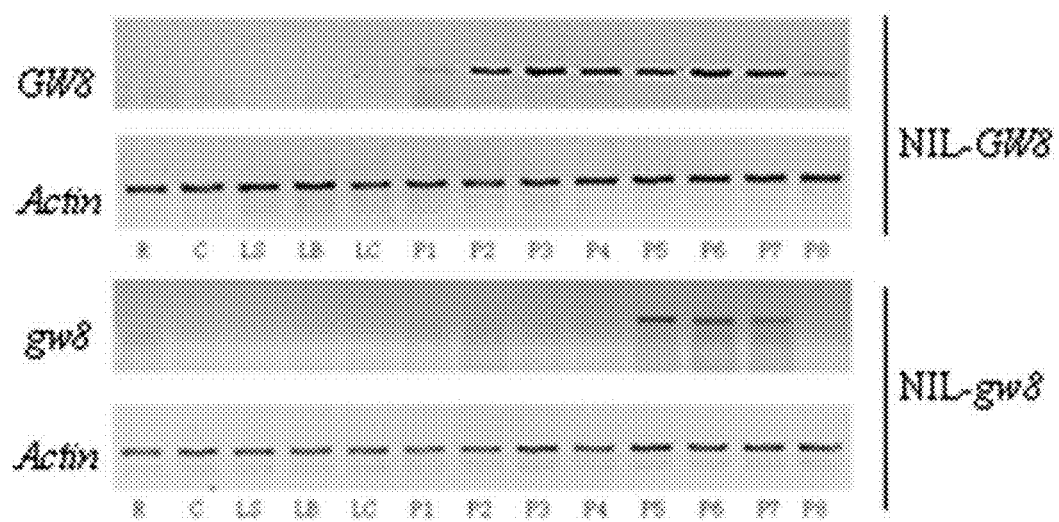

FIG. 3 shows the RT-PCR expression level comparison of GW8 gene in near-isogenic line NIL-GW8 and NIL-gw8. R refers to the root; C refers to the culm; LB blades; LS sheaths; LC leaves pad; P1-P8 refer to young panicle length of 1 cm, 2 cm, 3 cm, 7 cm, 9 cm, 13 cm, 16 cm and 23 cm.

Figure 4:
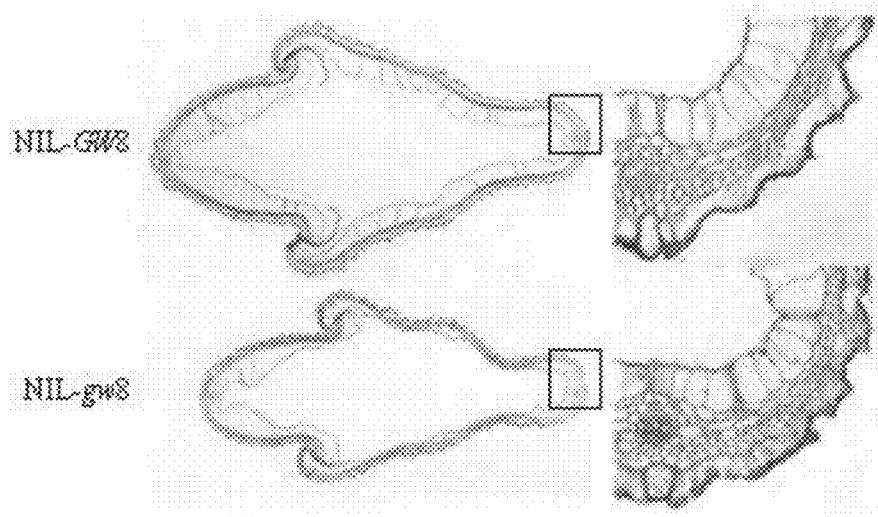

FIG. 4 shows the chaff cross-section comparison of near-isogenic lines NIL-GW8 and NIL-gw8.

Figure 5:
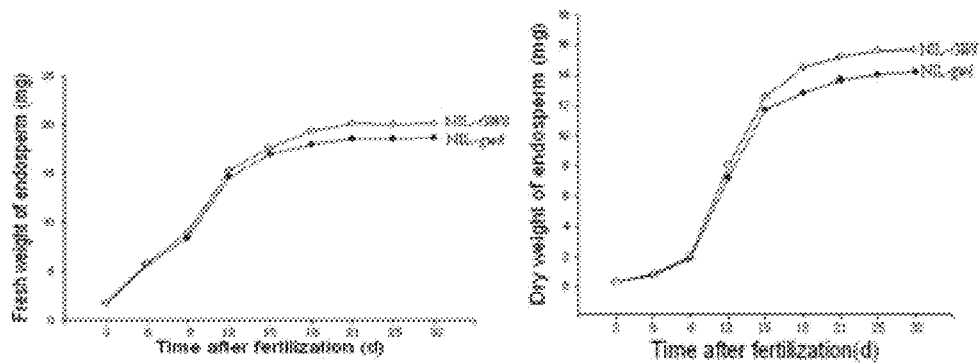

FIG. 5 shows the near-isogenic line NIL-GW8 and of NIL-gw8 grouting rate comparison; the left shows the changes of near-isogenic lines fresh weight of the seeds in the grouting process. The figure shows the near-isogenic lines seed in the grouting process by dry weight.

Figure 6:
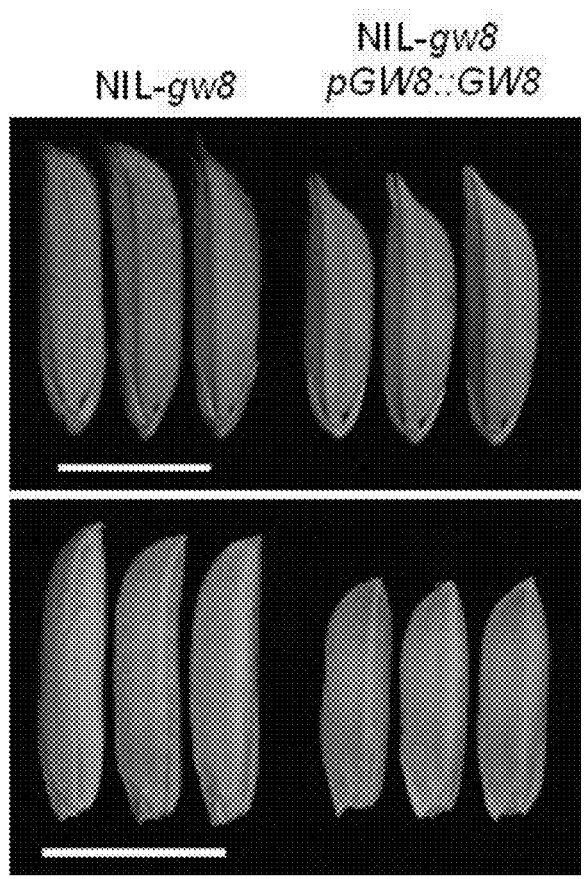

FIG. 6 shows genetic complementation for GW8 function. GW8 gene expression in the NIL-gw8 plants resulted in an increase in the grain width and changed the aspect ratio. Overexpression of the GW8 gene lead to the change of the size of a grain of rice.

Figure 7:
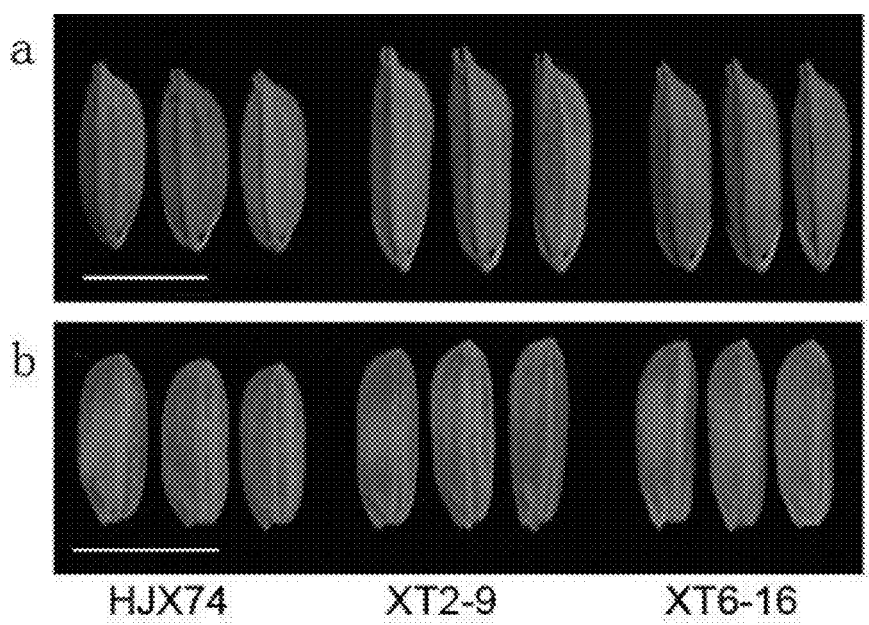

FIG. 7 shows that the reduced GW8 gene expression in NIL-GW8 transgenic plants appropriately changed the grain width and improved the aspect ratio. HJX74 refers the Huajingxian 74 parents (NIL-GW8), XT2-9 and XT6-16 refer to the two independent transgenic rice lines carrying RNAi-GW8. This figure shows that down-regulating the GW8 gene expression increased seed size and changed the aspect ratio; changed the grain type.

Figure 8:
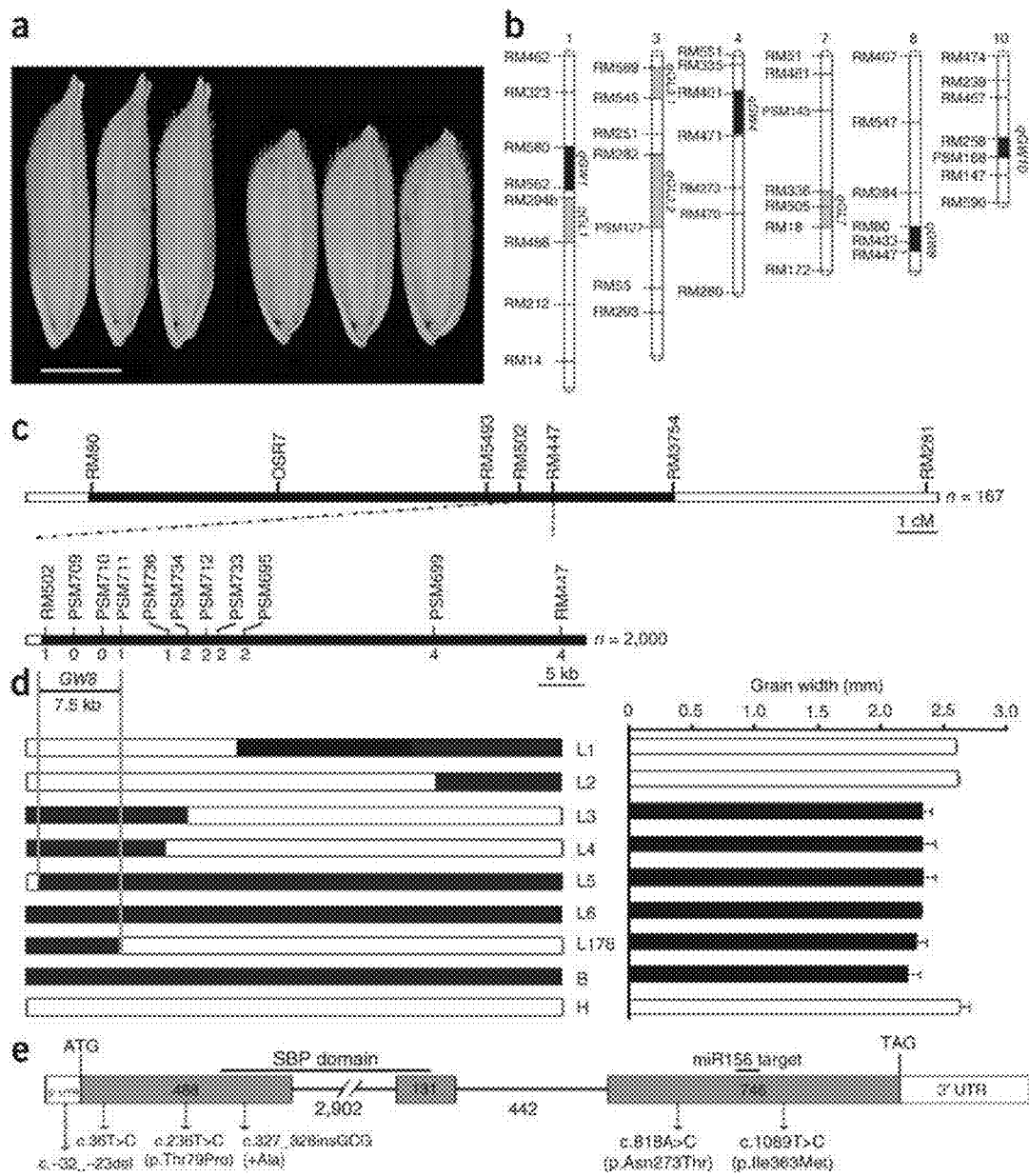

FIG. 8 shows (a) Parental grains. Scale bar, 3 mm. (b) QTL locations for grain length (GL) and width (GW) derived from the cross between Basmati385 and HJX74. (c) In the fine-scale map generated from analysis of 2,000 F2 segregants, the QTL falls in the interval between RM502 and PSM736. Numbers below the line indicate the number of recombinants between qGW8 and the marker shown. (d) Genotyping of progeny homozygous for qGW8 delimited the locus to an ~7.5-kb stretch flanked by RM502 and PSM711. Grain width (mean±standard error (SE), n=30) of recombinant BC5F4 lines (L1-L6), a BC6F3 line (L178) and the two parental varieties (H, HJX74; B, Basmati385). Filled and open bars represent chromosomal segments homozygous for Basmati385 and HJX74 alleles, respectively. (e) Mapping of allelic variation to the Basamti385 OsSPL16 protein sequence.

FIG. 9 shows (a-d) Grains from transgenic NIL-GW8 (a), NIL-gw8 (b), NIL-gw8 (c) and Basmati385 (d) plants. Scale bars, 2.5 mm. (e) Expression of OsSPL16 in NIL-GW8 and NIL-gw8. R, root; C, culm; L, leaf blade; SAM, shoot apex meristem; BM, branch meristem; YP1-Y22, young panicles, where the number indicates the length of the panicle in centimeters. Expression levels are shown as relative number of copies per 1,000 copies of rice actin3. Data are given as mean±s.e.m. (n=4). (f) Spikelets of NIL-GW8 and NIL-gw8 plants before anthesis. Scale bar, 2.5 mm. (g) Cross-sections of spikelet hulls indicated by the dashed line in f. Scale bar, 0.5 mm. (h) Magnified view of the cross-section boxed in g. Scale bar, 100 μm. (i-k) Total length (i), cell number (j) and cell length (k) in the outer parenchyma layer of the spikelet hulls formed by NIL-GW8 and NIL-gw8. Data are given as mean±s.e.m. (n=12). Student's t tests were used to generate P values.

FIG. 10 shows (a) Mature plant appearance. Scale bar, 10 cm. (b) NIL-GW8 and NIL-gw8 grains. Scale bar, 2.5 mm. (c) Plant height. (d) Tiller number. (e) Panicle length. (f) Number of secondary branches per panicle. (g) Number of grains per panicle. (h) Grain length. (i) Grain width. (j) 1,000-grain weight. (k) Grain yield per plot. All phenotypic data in c-k were measured from plants grown with 20×20 cm spacing in paddies under normal cultivation conditions. Data represent mean±s.e.m. (n=120). Student's t tests were used to generate P values.

FIG. 11 shows (a) Appearance of the grain formed by Basmati385 and various NILs. Scale bar, 3 mm. (b) The QTL content of the NILs. Chromosomal segments homozygous with respect to Basmati385 are shown as filled bars, and those homozygous with respect to HJX74 are shown as empty bars. (c) Grain width. (d) Grain length. (e) 1,000-grain weight. Data in c-e are given as mean±s.e.m. (n=40). (f) Polymorphism at the OsmiR156 target site within OsSPL16 in the Amol3 variety. (g) Expression analysis of OsSPL16 in NIL-gw8$^{Amol}$. Abbreviations are as in FIG. 9. Relative expression is shown as the number of copies per 1,000 copies of rice actin3. Data are given as mean±s.e.m. (n=4). (h) Grains from NIL-gw8$^{Amol}$ plants. Scale bar, 2.5 mm. (i-k) Contrast between NIL-GW8 and NIL-gw8$^{Amol}$ with respect to 1,000-grain weight (i), the number of grains per panicle (j) and grain yield per plot (k). All phenotypic data were measured from field-grown plants under normal cultivation conditions. Data are given as mean±s.e.m. (n=120). Student's t tests were used to generate P values.

FIG. 12 shows the effect of OsSPL16 on the physicochemical characteristics of milled rice.

DETAILED DESCRIPTION OF THE DISCLOSURE

Grain size and shape are important components of grain yield and quality and have been under selection since cereals were first domesticated. A quantitative trait locus GW8 is synonymous with OsSPL16, which encodes a protein that is a positive regulator of cell proliferation. Higher expression of this gene promotes cell division and grain filling, with positive consequences for grain width and yield in rice. Conversely, a loss-of-function mutation in Basmati rice is associated with the formation of a more slender grain and better quality of appearance. The correlation between grain size and allelic variation at the GW8 locus demonstrates that mutations within the promoter region are used to select the desirable alleles in rice breeding programs. A marker-assisted approach targeted at elite alleles of GS3 and OsSPL16 underlying grain size and shape are effectively used to simultaneously improve grain quality and yield.

Basmati rice offers superior grain quality, but the yield is lower. It was analyzed whether the Basmati gw8 allele could be used to improve grain quality. Down-regulation of OsSPL16 in NIL-GW8 plants produced better appearance quality in terms of the grain length-to-width ratio, endosperm transparency and the percentage of grain with chalkiness (FIG. 12). In contrast, increasing expression of OsSPL16 caused a reduction in the length-to-width ratio, with negative consequences for the appearance of the grain in both transgenic Basmati385 and NIL-gw8 plants (FIG. 12). Chalky endosperm was filled with loosely packed and spherical starch granules, whereas translucent endosperm had tightly packed and polyhedral starch granules. Analysis with scanning electron microscopy showed that the NIL-gw8 endosperm comprised largely sharp-edged, compactly arranged polygonal starch granules, which is consistent with the low extent of grain chalkiness. Thus, the Basmati gw8 allele produces a better quality grain, whereas the HJX74 GW8 allele enhances grain yield.

Haplotype diversity of the OsSPL16 sequence (including the promoter, transcript and 3' UTR) was conducted with a representative panel of 115 modern cultivars, landraces and wild progenitors. Sequence variation within the coding region was common, but three haplotype groups were distinguished, namely Basmati, HJX74 and TN-1. The 16 wild accessions (*Oryza rufipogon* and *O. nivara*) belonged to either the HJX74 or the Basmati haplotype, as did the indica landraces. All Basmati accessions carried the Basmati haplotype, while none of the high-yield indica cultivars did so. This outcome indicates that the Basmati haplotype was retained because of its association with better grain quality, whereas the HJX74 haplotype was selected for higher grain productivity in elite indica varieties.

qGS3 is a major determinant of grain length in Basmati rice (FIG. 8b), and sequence variation in the GS3 locus showed that Basmati385 has the same mutation as Minghui63. Thus, its interaction with qGW8 was of interest. The four contrasting allelic combinations of qGS3 and qGW8 were assembled into a near-isogenic (HJX74) background. NIL-GW8/gs3 plants possessing the qgs3 allele from Basmati385 produced longer and heavier grains than those from NIL-GW8/GS3 control plants (FIG. 11a-e), whereas NIL-gw8/gs3 plants carrying both the qgw8 and qgs3 alleles from Basmati385 formed grains that were narrower and more slender than those formed by NIL-GW8/gs3 plants (FIG. 11a,c). The size and shape of the grains produced by NIL-gw8/gs3 plants were similar to the characteristics of grains produced by Basmati385 itself (FIG. 11c-e). By designed QTL pyramiding based on combinations of qgw8 and qgs3 alleles with molecular marker-assisted selection, a new elite indica variety, Huabiao1, was developed with substantially improved grain quality and similar yields to HJX74.

Figures 10A, 10B:
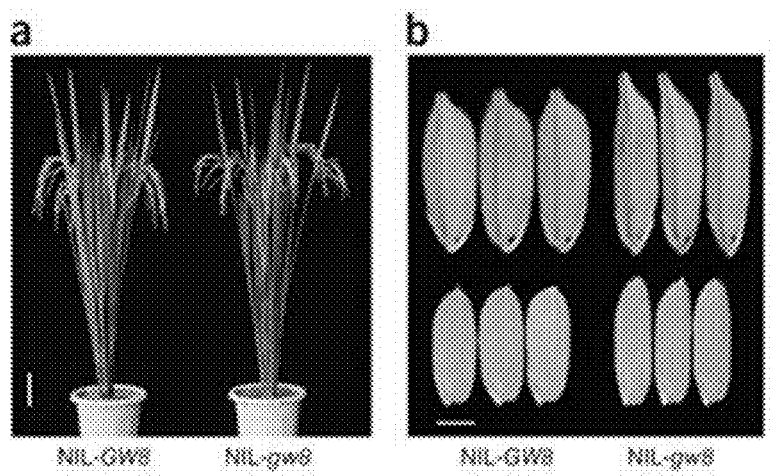
Figure 10C:
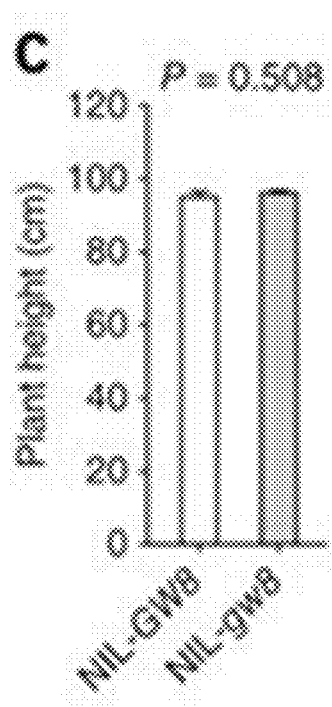
Figure 10D:
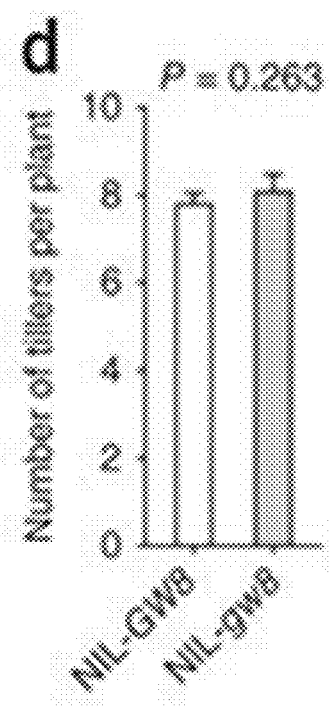
Figure 10E:
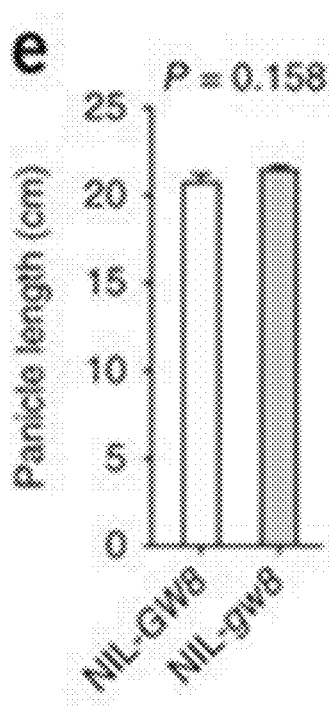
Figure 10F:
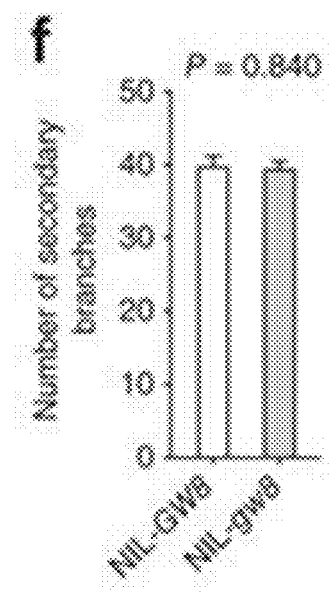
Figure 10G:
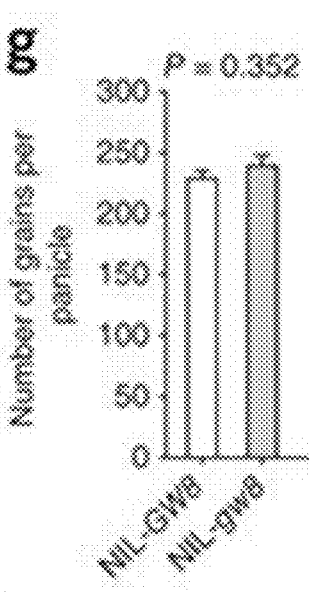
Figure 10H:
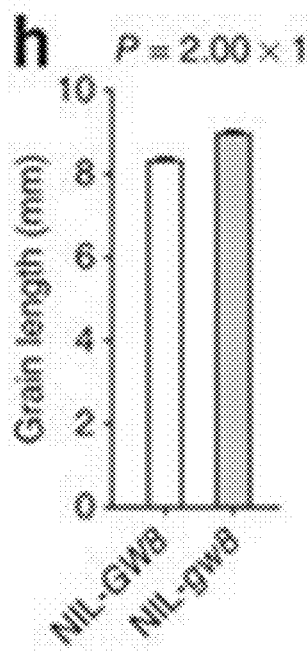
Figure 10I:
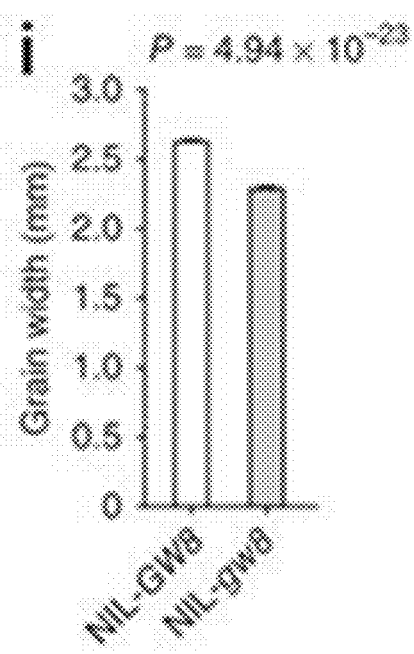
Figure 10J:
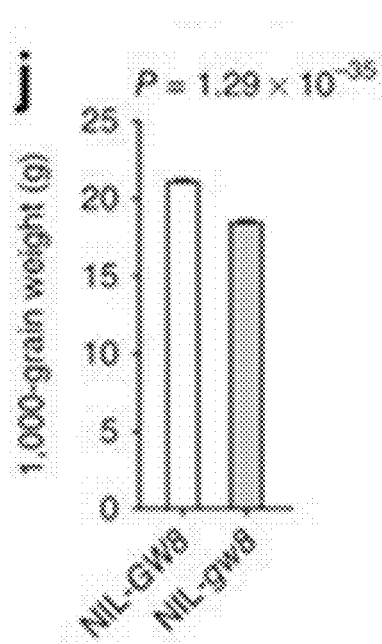
Figure 10K:
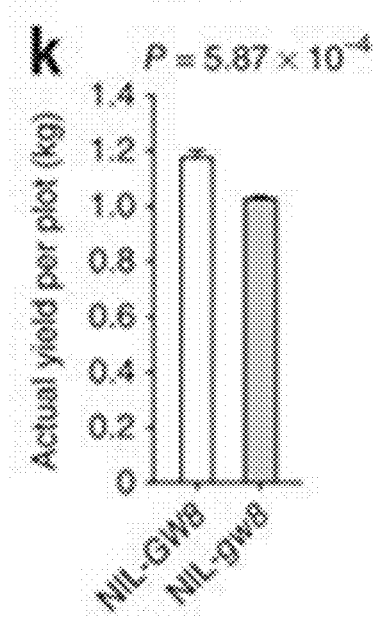
Figure 11F:
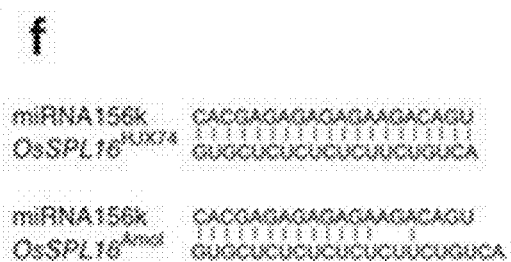
Figure 11G:
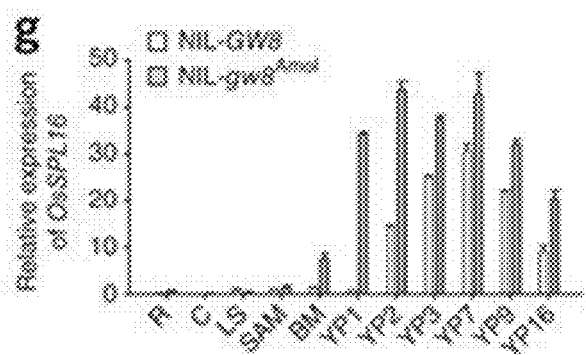
Figure 11H:
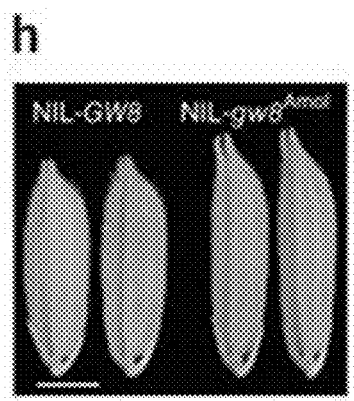
Figure 11I:
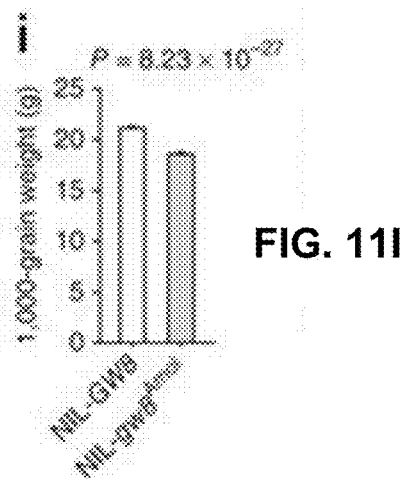
Figures 11J, 11K:
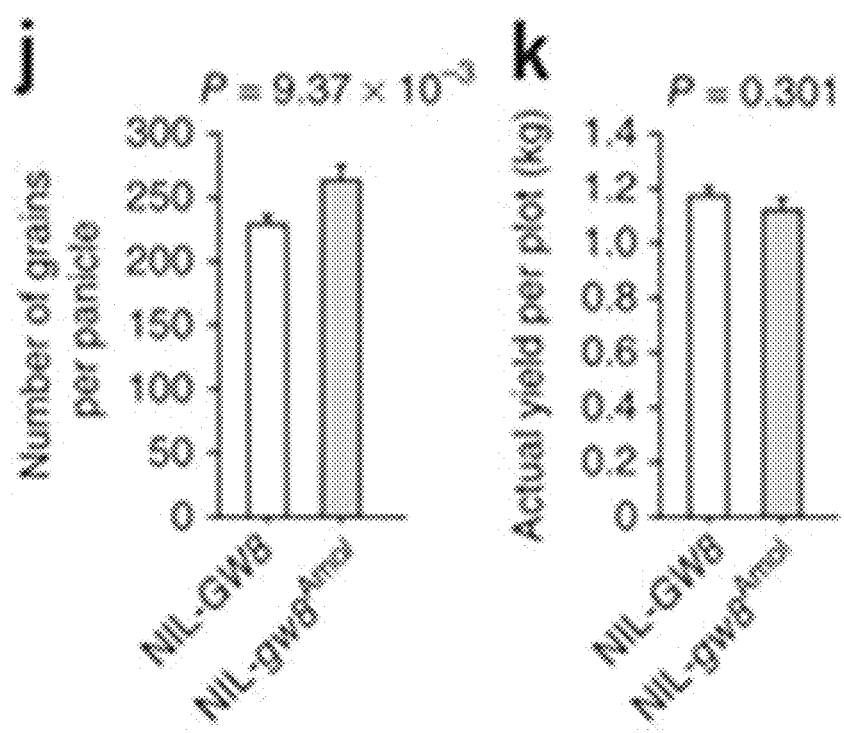

An allelic variant found in the Iranian rice cultivar Amol3 has a 2 bp indel at its OsSPL16 OsmiR156 target site (FIG. 11f). This cultivar was therefore used to breed NIL-gw8$^{Amol}$, a line which contains a short chromosome segment inherited from Amol3 in the HJX74 genetic background. Expression analysis showed that, during the reproductive stage, the expression of OsSPL16 was higher in NIL-gw8$^{Amol}$ than that in NIL-GW8 plants (FIG. 11g). NIL-gw8$^{Amol}$ plant formed a particularly slender grain (FIG. 11h,i), and developed higher grain numbers than NIL-GW8 ones (FIG. 11j). Under field conditions, the grain yield of NIL-gw8$^{Amol}$ and NIL-GW8 plants was indistinguishable (FIG. 11k), however, NIL-gw8$^{Amol}$ plants were 13.5% more productive than NIL-gw8 ones (FIG. 10k,11j). This outcome indicates that the gw8 allele was associated with an increase of ~14% in the grain yield per plant when were compared to the Basmati qgw8 allele.

The practice of the present disclosure will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982) *Botany: Plant Biology and Its Relation to Human Affairs*, John Wiley; *Cell Culture and Somatic Cell Genetics of Plants*, vol. 1, Vasil, ed. (1984); Stanier, et al., (1986) *The Microbial World*, 5$^{th}$ ed., Prentice-Hall; Dhringra and Sinclair, (1985) *Basic Plant Pathology Methods*, CRC Press; Maniatis, et al., (1982) *Molecular Cloning: A Laboratory Manual; DNA Cloning*, vols. I and II, Glover, ed. (1985); *Oligonucleotide Synthesis*, Gait, ed. (1984); *Nucleic Acid Hybridization*, Hames and Higgins, eds. (1984) and the series *Methods in Enzymology*, Colowick and Kaplan, eds, Academic Press, Inc., San Diego, Calif.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS) and strand displacement amplification (SDA). See, e.g., *Diagnostic Molecular Microbiology: Principles and Applications*, Persing, et al., eds., American Society for Microbiology, Washington, D.C. (1993). The product of amplification is termed an amplicon.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N terminal and C terminal portions of the polypeptide molecule would also not be expected to alter the activity of the polypeptide. Each of the proposed modifications is well within the routine skill in the art, as is determination of retention of biological activity of the encoded products.

The protein disclosed herein may also be a protein which comprises an amino acid sequence comprising deletion, substitution, insertion and/or addition of one or more amino acids in an amino acid sequence selected from the group consisting of SEQ ID NO: 9 or variants thereof. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Proteins derived by amino acid deletion, substitution, insertion and/or addition can be prepared when DNAs encoding their wild-type proteins are subjected to, for example, well-known site-directed mutagenesis (see, e.g., Nucleic Acid Research, Vol. 10, No. 20, p. 6487-6500, 1982, which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-directed mutagenesis mentioned above, as well as other techniques such as those for treating a gene with a mutagen, and those in which a gene is selectively cleaved to remove, substitute, insert or add a selected nucleotide or nucleotides, and then ligated.

The protein disclosed herein may also be a protein which is encoded by a nucleic acid comprising a nucleotide sequence comprising deletion, substitution, insertion and/or addition of one or more nucleotides in a nucleotide sequence selected from the group consisting of SEQ ID NOS: 1-6. Nucleotide deletion, substitution, insertion and/or addition may be accomplished by site-directed mutagenesis or other techniques as mentioned above.

The protein disclosed herein may also be a protein which is encoded by a nucleic acid comprising a nucleotide sequence hybridizable under stringent conditions with the complementary strand of a nucleotide sequence selected from the group consisting of SEQ ID NOS: 1-6.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system. Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (Yamao, et al., (1985) *Proc. Natl. Acad. Sci. USA* 82:2306-9) or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present disclosure may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the disclosure, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "nitrate uptake-associated nucleic acid" means a nucleic acid comprising a polynucleotide ("nitrate uptake-associated polynucleotide") encoding a full length or partial length nitrate uptake-associated polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) *Guide To Molecular Cloning Techniques*, from the series *Methods in Enzymology*, vol. 152, Academic Press, Inc., San Diego, Calif.; Sambrook, et al., (1989) *Molecular Cloning: A Laboratory Manual*, $2^{nd}$ ed., vols. 1-3; and *Current Protocols in Molecular Biology*, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter, and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the disclosure, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is *Zea mays*.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTPIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Pasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTPIT, BLAST®, PASTA and TFASTA in the Wisconsin Genetics Software Package, Version 8 (available from Genetics Computer Group (GCG® programs (Accelrys, Inc., San Diego, Calif.)). The CLUSTAL program is well described by Higgins and Sharp, (1988) *Gene* 73:237-44; Higgins and Sharp, (1989) *CABIOS* 5:151-3; Carpet, et al., (1988) *Nucleic Acids Res.* 16:10881-90; Huang, et al., (1992) *Computer Applications in the Biosciences* 8:155-65 and Pearson, et al., (1994) *Meth. Mol. Biol.* 24:307-31. The preferred program to use for optimal global alignment of multiple sequences is Pile Up (Feng and Doolittle, (1987) *J. Mol. Evol.,* 25:351-60 which is similar to the method described by Higgins and Sharp, (1989) *CABIOS* 5:151-53 and hereby incorporated by reference). The BLAST® family of programs which can be used for database similarity searches includes: BLASTN for nucleotide query sequences against nucleotide database sequences;

BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, *Current Protocols in Molecular Biology*, Chapter 19, Ausubel et al., eds., Greene Publishing and Wiley-Interscience, NewYork (1995).

As those of ordinary skill in the art will understand, BLAST® searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low complexity alignments. For example, the SEG (Wooten and Federhen, (1993) *Comput. Chem.* 17:149-63) and XNU (Claverie and States, (1993) *Comput. Chem.* 17:191-201) low complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Variant Nucleotide Sequences in the Non-Coding Regions

The nitrate uptake-associated nucleotide sequences are used to generate variant nucleotide sequences having the nucleotide sequence of the 5'-untranslated region, 3'-untranslated region or promoter region that is approximately 70%, 75%, 80%, 85%, 90% and 95% identical to the original nucleotide sequence of the corresponding SEQ ID NO: 1. These variants are then associated with natural variation in the germplasm for component traits related to grain quality and/or grain yield. The associated variants are used as marker haplotypes to select for the desirable traits.

Variant Amino Acid Sequences of OsSPL16-Associated Polypeptides

Variant amino acid sequences of OsSPL16-associated polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined herein is followed. Variants having about 70%, 75%, 80%, 85%, 90% and 95% nucleic acid sequence identity are generated using this method. These variants are then associated with natural variation in the germplasm for component traits related to grain quality and/or grain yield. The associated variants are used as marker haplotypes to select for the desirable traits.

Synthetic Methods for Constructing Nucleic Acids

The isolated nucleic acids of the present disclosure can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20):1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68 and the solid support method of U.S. Pat. No. 4,458,066.

Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present disclosure provides 5' and/or 3' UTR regions for modulation of translation of heterologous coding sequences.

Plant Transformation Methods

Numerous methods for introducing foreign genes into plants are known and can be used to insert a nitrate uptake-associated polynucleotide into a plant host, including biological and physical plant transformation protocols. See, e.g., Miki, et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., (1985) *Science* 227:1229-31), electroporation, microinjection and biolistic bombardment.

Expression cassettes and vectors and in vitro culture methods for plant cell or tissue transformation and regeneration of plants are known and available. See, e.g., Gruber et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, i.e., monocot or dicot, targeted for gene modification. Suitable methods of transforming plant cells include microinjection (Crossway, et al., (1986) *Biotechniques* 4:320-334 and U.S. Pat. No. 6,300,543), electroporation (Riggs, et al., (1986) *Proc. Natl. Acad. Sci. USA* 83:5602-5606, direct gene transfer (Paszkowski, et al., (1984) *EMBO J.* 3:2717-2722) and ballistic particle acceleration (see, for example, Sanford, et al., U.S. Pat. No. 4,945,050; WO 91/10725 and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods*. eds. Gamborg and Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839 and Gordon-Kamm, et al., (1990) *Plant Cell* 2:603-618 (maize); Hooydaas-Van Slogteren and Hooykaas (1984) *Nature* (London) 311:763-764; Bytebierm, et al., (1987) *Proc. Natl. Acad. Sci. USA* 84:5345-5349 (Liliaceae); De Wet, et al., (1985) *In The Experimental Manipulation of Ovule Tissues*, ed. Chapman, et al., pp. 197-209. Longman, NY (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185), all of which are herein incorporated by reference.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion or via a binary system where the vir gene is present on a separate vector. Such systems, vectors for use therein, and methods of transforming plant cells are described in U.S. Pat. No. 4,658,082; U.S. patent application Ser. No. 913,914, filed Oct. 1, 1986, as referenced in U.S. Pat. No. 5,262,306, issued Nov. 16, 1993 and Simpson, et al., (1986)

*Plant Mol. Biol.* 6:403-15 (also referenced in the '306 patent), all incorporated by reference in their entirety.

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. patent application Ser. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206 and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731 and Christou, et al., (1987) *Proc. Natl. Acad. Sci. USA* 84:3962. Direct uptake of DNA into protoplasts using $CaCl_2$ precipitation, polyvinyl alcohol or poly-L-ornithine has also been reported. See, e.g., Hain, et al., (1985) *Mol. Gen. Genet.* 199:161 and Draper, et al., (1982) *Plant Cell Physiol.* 23:451.

Electroporation of protoplasts and whole cells and tissues has also been described. See, e.g., Donn, et al., (1990) *Abstracts of the VIIth Int'l. Congress on Plant Cell and Tissue Culture IAPTC*, A2-38, p. 53; D'Halluin, et al., (1992) *Plant Cell* 4:1495-505 and Spencer, et al., (1994) *Plant Mol. Biol.* 24:51-61.

Reducing the Activity and/or Level of Components Involved in Traits Related to Grain Quality and/or Grain Yield Methods are provided to reduce or eliminate the activity by transforming a plant cell with an expression cassette that expresses a polynucleotide that down-regulates the expression of OsSPL16. The polynucleotide may inhibit the expression of OsSPL16-associated polypeptide directly, by preventing transcription or translation of OsSPL16 messenger RNA or indirectly, by encoding a polypeptide that inhibits the transcription or translation of OsSPL16. Methods for inhibiting or eliminating the expression of a gene in a plant are well known in the art, and any such method may be used in the present disclosure to inhibit the expression of OsSPL16. Many methods may be used to reduce or eliminate the activity of OsSPL16. In addition, more than one method may be used to reduce the activity of OsSPL16.

1. Polynucleotide-Based Methods:

In some embodiments of the present disclosure, a plant is transformed with an expression cassette that is capable of expressing a polynucleotide that inhibits the expression of OsSPL16 of the disclosure. The term "expression" as used herein refers to the biosynthesis of a gene product, including the transcription and/or translation of said gene product. For example, for the purposes of the present disclosure, an expression cassette capable of expressing a polynucleotide that inhibits the expression of at least one nitrate uptake-associated polypeptide is an expression cassette capable of producing an RNA molecule that inhibits the transcription and/or translation of at least one nitrate uptake-associated polypeptide of the disclosure. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of OsSPL16 are given below.

i. Sense Suppression/Cosuppression

In some embodiments of the disclosure, inhibition of the expression of OsSPL16 may be obtained by sense suppression or cosuppression. For cosuppression, an expression cassette is designed to express an RNA molecule corresponding to all or part of a messenger RNA encoding OsSPL16 in the "sense" orientation. Over expression of the RNA molecule can result in reduced expression of the native gene. Accordingly, multiple plant lines transformed with the cosuppression expression cassette are screened to identify those that show the greatest inhibition of nitrate uptake-associated polypeptide expression.

The polynucleotide used for cosuppression may correspond to all or part of the sequence encoding the nitrate uptake-associated polypeptide, all or part of the 5' and/or 3' untranslated region of OsSPL16 transcript or all or part of both the coding sequence and the untranslated regions of a transcript encoding OsSPL16. In some embodiments where the polynucleotide comprises all or part of the coding region for the nitrate uptake-associated polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

ii. Antisense Suppression

In some embodiments of the disclosure, inhibition of the expression of the nitrate uptake-associated polypeptide may be obtained by antisense suppression. For antisense suppression, the expression cassette is designed to express an RNA molecule complementary to all or part of a messenger RNA encoding the nitrate uptake-associated polypeptide. Over expression of the antisense RNA molecule can result in reduced expression of the native gene. Accordingly, multiple plant lines transformed with the antisense suppression expression cassette are screened to identify those that show the greatest inhibition of nitrate uptake-associated polypeptide expression.

The polynucleotide for use in antisense suppression may correspond to all or part of the complement of the sequence encoding the nitrate uptake-associated polypeptide, all or part of the complement of the 5' and/or 3' untranslated region of the nitrate uptake-associated transcript or all or part of the complement of both the coding sequence and the untranslated regions of a transcript encoding the nitrate uptake-associated polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the disclosure, inhibition of the expression of OsSPL16 may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of nitrate uptake-associated polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743 and WO 99/49029, WO 99/53050, WO 99/61631 and WO 00/49035, each of which is herein incorporated by reference.

iv. Hairpin RNA Interference and Intron-Containing Hairpin RNA Interference

In some embodiments of the disclosure, inhibition of the expression of OsSPL16 may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7, and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods*

30:289-295 and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904; Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Nat'l. Acad. Sci.* 99(4):16499-16506; Sijen, et al., *Curr. Biol.* (2001) 11:436-440), herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the nitrate uptake-associated polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the disclosure is catalytic RNA or has ribozyme activity specific for the messenger RNA of the nitrate uptake-associated polypeptide. Thus, the polynucleotide causes the degradation of the endogenous messenger RNA, resulting in reduced expression of the nitrate uptake-associated polypeptide. This method is described, for example, in U.S. Pat. No. 4,987,071, herein incorporated by reference.

vii. Small Interfering RNA or Micro RNA

In some embodiments of the disclosure, inhibition of the expression of OsSPL16 may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of nitrate uptake-associated expression, the 22-nucleotide sequence is selected from a nitrate uptake-associated transcript sequence and contains 22 nucleotides of said nitrate uptake-associated sequence in sense orientation and 21 nucleotides of a corresponding antisense sequence that is complementary to the sense sequence. miRNA molecules are highly efficient at inhibiting the expression of endogenous genes and the RNA interference they induce is inherited by subsequent generations of plants.

2. Polypeptide-Based Inhibition of Gene Expression

In one embodiment, the polynucleotide encodes a zinc finger protein that binds to a gene encoding OsSPL16, resulting in reduced expression of the gene. In particular embodiments, the zinc finger protein binds to a regulatory region of a nitrate uptake-associated gene. In other embodiments, the zinc finger protein binds to a messenger RNA encoding OsSPL16 and prevents its translation. Methods of selecting sites for targeting by zinc finger proteins have been described, for example, in U.S. Pat. No. 6,453,242 and methods for using zinc finger proteins to inhibit the expression of genes in plants are described, for example, in US. Patent Application Publication Number 2003/0037355, each of which is herein incorporated by reference.

3. Polypeptide-Based Inhibition of Protein Activity

In some embodiments of the disclosure, the polynucleotide encodes an antibody that binds to at least one nitrate uptake-associated polypeptide and reduces the enhanced nitrogen utilization activity of the nitrate uptake-associated polypeptide. In another embodiment, the binding of the antibody results in increased turnover of the antibody-nitrate uptake-associated complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present disclosure, the activity of OsSPL16 is reduced or eliminated by disrupting the gene encoding the nitrate uptake-associated polypeptide. The gene encoding the nitrate uptake-associated polypeptide may be disrupted by any method known in the art. For example, in one embodiment, the gene is disrupted by transposon tagging. In another embodiment, the gene is disrupted by mutagenizing plants using random or targeted mutagenesis and selecting for plants that have reduced nitrogen utilization activity.

i. Transposon Tagging

In one embodiment of the disclosure, transposon tagging is used to reduce or eliminate the nitrate uptake-associated activity of one or more nitrate uptake-associated polypeptide. Transposon tagging comprises inserting a transposon within an endogenous nitrate uptake-associated gene to reduce or eliminate expression of the nitrate uptake-associated polypeptide. "nitrate uptake-associated gene" is intended to mean the gene that encodes OsSPL16 according to the disclosure.

In this embodiment, the expression of one or more nitrate uptake-associated polypeptide is reduced or eliminated by inserting a transposon within a regulatory region or coding region of the gene encoding the nitrate uptake-associated polypeptide. A transposon that is within an exon, intron, 5' or 3' untranslated sequence, a promoter or any other regulatory sequence of a nitrate uptake-associated gene may be used to reduce or eliminate the expression and/or activity of the encoded nitrate uptake-associated polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell*

7:75-84; Mena, et al., (1996) *Science* 274:1537-1540 and U.S. Pat. No. 5,962,764, each of which is herein incorporated by reference.

ii. Mutant Plants with Reduced Activity

Additional methods for decreasing or eliminating the expression of endogenous genes in plants are also known in the art and can be similarly applied to the instant disclosure. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243:472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant disclosure. See, McCallum, et al., (2000) *Nat. Biotechnol.* 18:455-457, herein incorporated by reference.

Mutations that impact gene expression or that interfere with the function (enhanced nitrogen utilization activity) of the encoded protein are well known in the art. Insertional mutations in gene exons usually result in null-mutants. Mutations in conserved residues are particularly effective in inhibiting the activity of the encoded protein. Conserved residues of plant nitrate uptake-associated polypeptides suitable for mutagenesis with the goal to eliminate nitrate uptake-associated activity have been described. Such mutants can be isolated according to well-known procedures, and mutations in different nitrate uptake-associated loci can be stacked by genetic crossing. See, for example, Gruis, et al., (2002) *Plant Cell* 14:2863-2882.

In another embodiment of this disclosure, dominant mutants can be used to trigger RNA silencing due to gene inversion and recombination of a duplicated gene locus. See, for example, Kusaba, et al., (2003) *Plant Cell* 15:1455-1467.

The disclosure encompasses additional methods for reducing or eliminating the activity of one or more nitrate uptake-associated polypeptide. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. See also, WO 98/49350, WO 99/07865, WO 99/25821 and Beetham, et al., (1999) *Proc. Natl. Acad. Sci. USA* 96:8774-8778, each of which is herein incorporated by reference.

vi. Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the nitrate uptake-associated polypeptide has not been modulated. "Modulating floral development" further includes any alteration in the timing of the development of a plant's reproductive tissue (i.e., a delayed or an accelerated timing of floral development) when compared to a control plant in which the activity or level of the nitrate uptake-associated polypeptide has not been modulated. Macroscopic alterations may include changes in size, shape, number, or location of reproductive organs, the developmental time period that these structures form or the ability to maintain or proceed through the flowering process in times of environmental stress. Microscopic alterations may include changes to the types or shapes of cells that make up the reproductive organs.

The method for modulating floral development in a plant comprises modulating nitrate uptake-associated activity in a plant. In one method, a nitrate uptake-associated sequence of the disclosure is provided. A nitrate uptake-associated nucleotide sequence can be provided by introducing into the plant a polynucleotide comprising a nitrate uptake-associated nucleotide sequence of the disclosure, expressing the nitrate uptake-associated sequence and thereby modifying floral development. In other embodiments, the nitrate uptake-associated nucleotide construct introduced into the plant is stably incorporated into the genome of the plant.

In specific methods, floral development is modulated by increasing the level or activity of the nitrate uptake-associated polypeptide in the plant. A change in nitrate uptake-associated activity can result in at least one or more of the following alterations in floral development, including, but not limited to, altered flowering, changed number of flowers, modified male sterility and altered seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S111-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters and inflorescence-preferred promoters.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases and those involved in housekeeping, such as heat shock proteins. More specific categories of transgenes, for example, include genes encoding important traits for agronomics, insect resistance, disease resistance, herbicide resistance, sterility, grain characteristics and commercial products. Genes of interest include, generally, those involved in oil, starch, carbohydrate, or nutrient metabolism as well as those affecting kernel size, sucrose loading, and the like.

In certain embodiments the nucleic acid sequences of the present disclosure can be used in combination ("stacked") with other polynucleotide sequences of interest in order to create plants with a desired phenotype.

The rice line Basmati385 was obtained from the China National Rice Research Institute. The lines Huajiangxian 74; W09-38-60-7-7; W06-40-48-06-02-03-02-03-1; W09-38-60-07-07-03-04-0049-16; and W02-15-01-08-14-05-01-32 were obtained from Hunan Agriculture University.

This disclosure can be better understood by reference to the following non-limiting examples. It will be appreciated by those skilled in the art that other embodiments of the disclosure may be practiced without departing from the spirit and the scope of the disclosure as herein disclosed and claimed.

EXAMPLES

Example 1—The Construction of GW8 Near-Isogenic Lines

Figure 1:
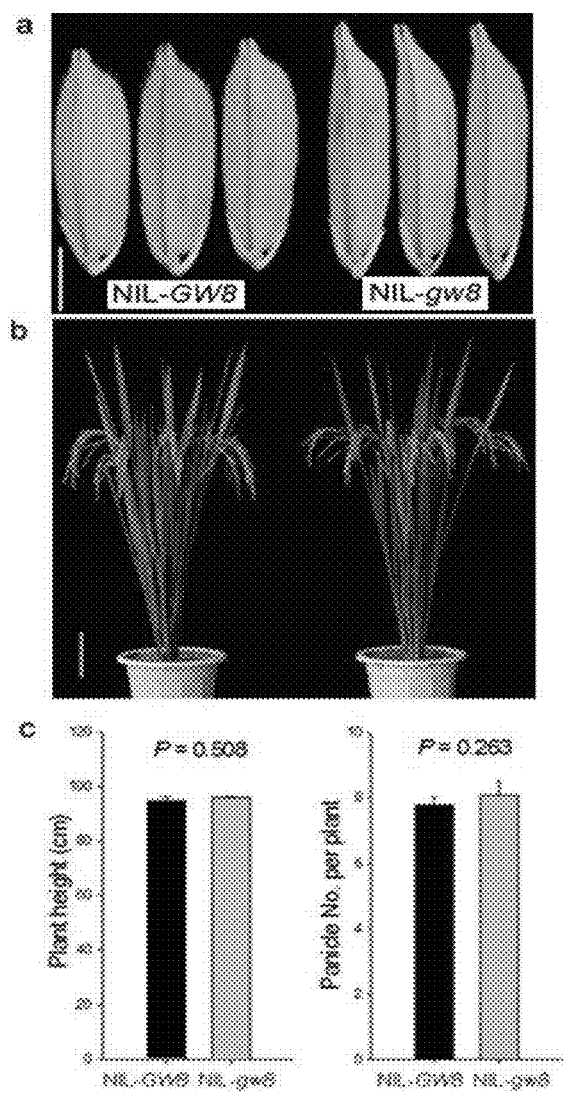
FIG. 1 shows the comparison of near-isogenic lines NIL-GW8 and NIL-gw8 compare. (A), grain shape and seed size comparison; (b), plant phenotype comparison; (c), plant height and effective panicles comparison.

High-yield rice variety Huajingxian74 (HJX74) was used as the recurrent parent and the slender grain Basmati385 were used as the donor parents and backcrossed (BC5F2) according to the narrowed grain width phenotype. Phenotype of near-isogenic lines the NIL-gw8 and the NIL-GW8 are shown in FIG. 1. Comparative analysis of phenotypes based on near-isogenic lines found little effect of GW8 genes on plant height, number of tillers, heading and per spike and grains per spike agronomic traits.

Figure 9A:
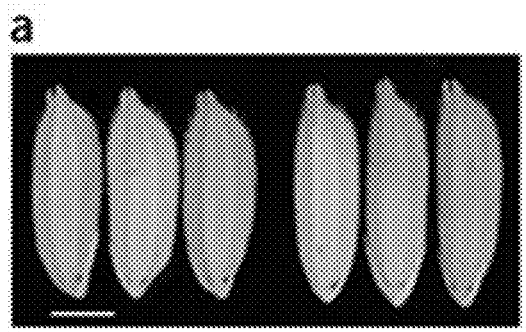
Figure 9B:
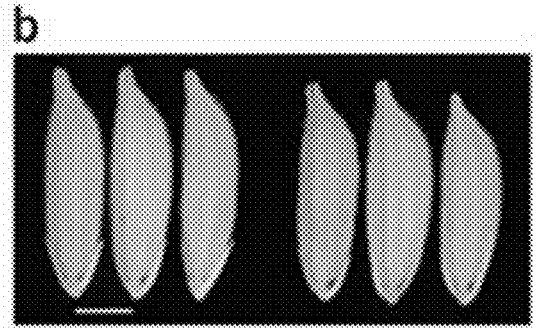
Figure 9C:
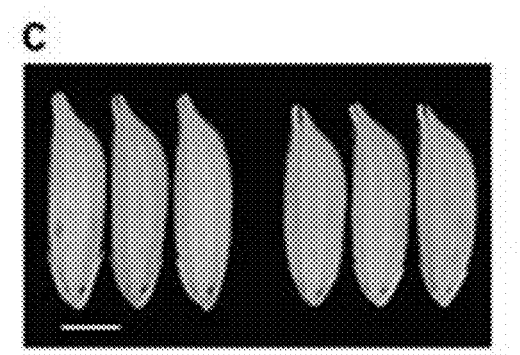
Figure 9D:
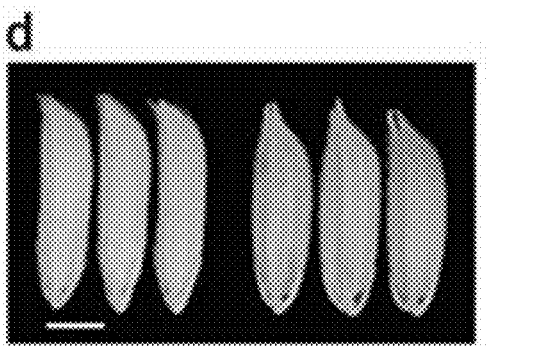

A near-isogenic line (NIL), NIL-gw8 that carries an ~407-kb segment including the Basmati385 qgw8 allele in the HJX74 background was developed. Its matching line, NIL-GW8, carries the homologous segment from HJX74. The constitutive expression of a small interfering RNA (siRNA) directed at OsSPL16 led to no visible change in phenotype at the whole-plant or panicle-architecture level, but all the transgenic NIL-GW8 plants formed grains that were substantially narrower and longer than those formed by non-transgenic NIL-GW8 plants (FIG. 9a). When the transgene construct included the HJX74 OsSPL16 cDNA, the transgenic NIL-gw8 plants formed grains that were significantly wider and shorter than those formed by non-transgenic NIL-gw8 plants (FIG. 9b). Grain width and length were also altered in NIL-gw8 plants expressing the Basmati385 OsSPL16 cDNA under the control of the native HJX74 promoter (FIG. 9c). Finally, Basmati385 plants expressing the Basmati385 OsSPL16 cDNA formed grains that were distinctly shorter and wider than those formed by non-transgenic Basmati385 plants (FIG. 9d). From these results, it was clear that none of the five polymorphisms in the coding region could be responsible for Basmati385 grain type.

Example 2—Comparative Study of GW8 Near-Isogenic Lines Panicle Traits

NIL-GW8 and the NIL-gw8 (nearly isogenic line NIL-GW8 and NIL-gw8) as described herein were tested (after successive backcrosses of 7 generation of near-isogenic lines). When the plants matured, the number of primary branches (primary branches, pb), the number of secondary branch (secondary branches, sb), panicle length (panicle length, PL), and grains per panicle number (number of Grains on each panicle) traits were measured as described in particular FIG. 2.

Statistical methods were used to measure the panicle-related traits. When the rice is mature in the field, about 30 main tiller spikes were taken into account. Statistics included on per panicle grain number (the number of grain per panicle), the number of primary branches (number of primary branches), times the rachis the number (number of secondary branches), panicle length (panicle length), direct counting and recording.

Grain type, grain weight measurements. Filled grains were dried at 37° C., stored at room temperature for more than three months and fully dried. Grain moisture content is relatively consistent. Morphologically normal seeds were randomly selected from each line. A vernier caliper was used to measure the grain width, grain length, grain shape observe other indicators. Grain weight was estimated based on 100 randomly selected full grains using an electronic balance by weighing the total weight.

Figure 2:
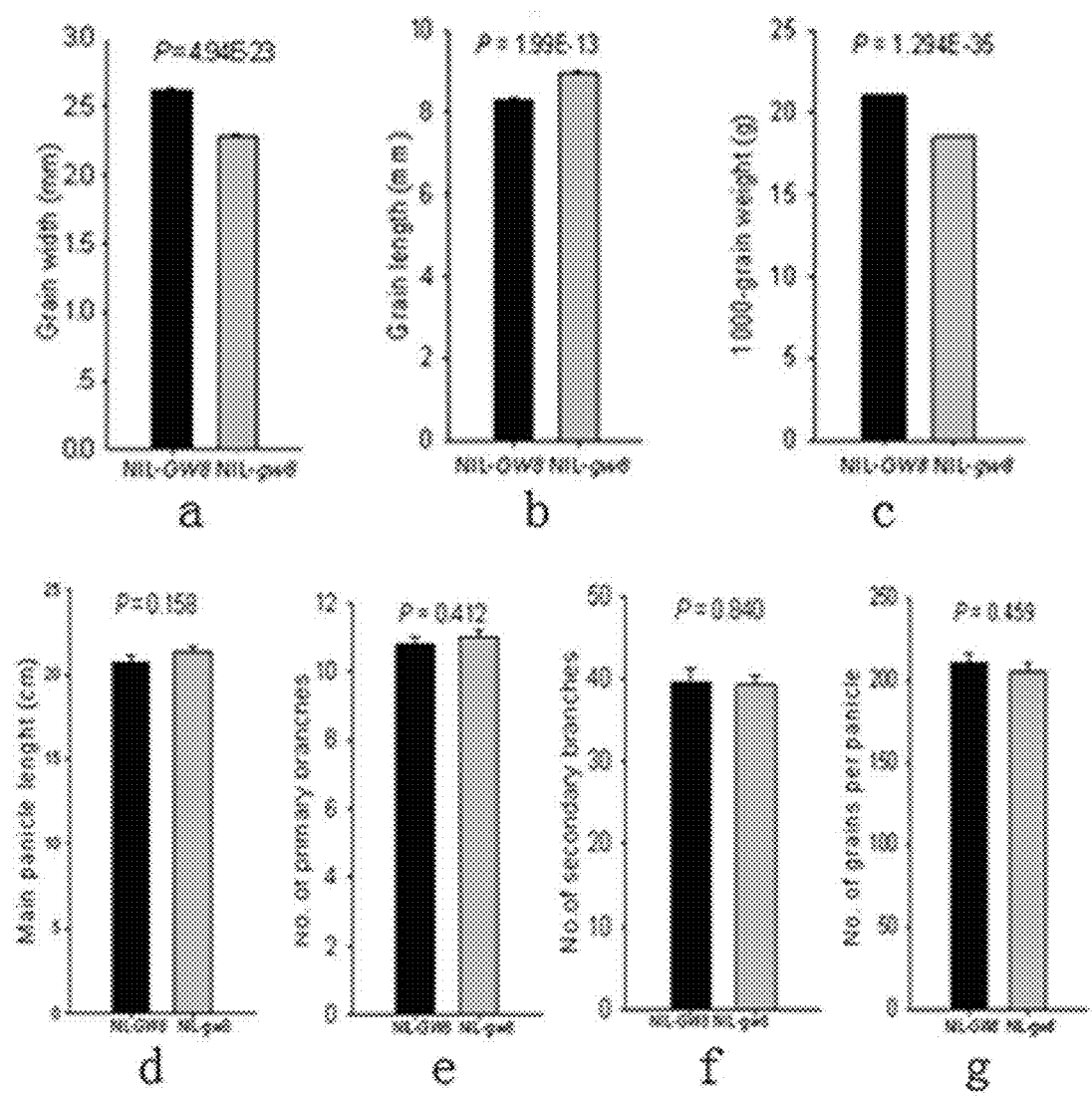
FIG. 2 shows the near-isogenic lines NIL-GW8 and the NIL-gw8 panicle phenotype comparison. (A), grain width; (b), grain length; (c), grain weight; (d), panicle length; (e) primary branch number comparison; (f), secondary branch number comparison; (g), comparison of the number of grain per panicle.

Statistics show that NIL-GW8 and NIL-gw8, there is no significant difference with respect to the spike length, number of primary branches, secondary branch number and the number of grain per ear (FIG. 2, d, e, f, and g). However, both grain width and grain length have significant. Similarly, grain weight difference of about 12% in NIL-GW8 than NIL-gw8 is highly significant (FIG. 2, a, b and c). Thus NIL-GW8 showed higher yield than NIL-gw8, indicates that wide grain rice varieties containing GW8 yield higher than varieties that contain gw8 (narrow grain) rice varieties to increase the yield potential.

Figure 9E:
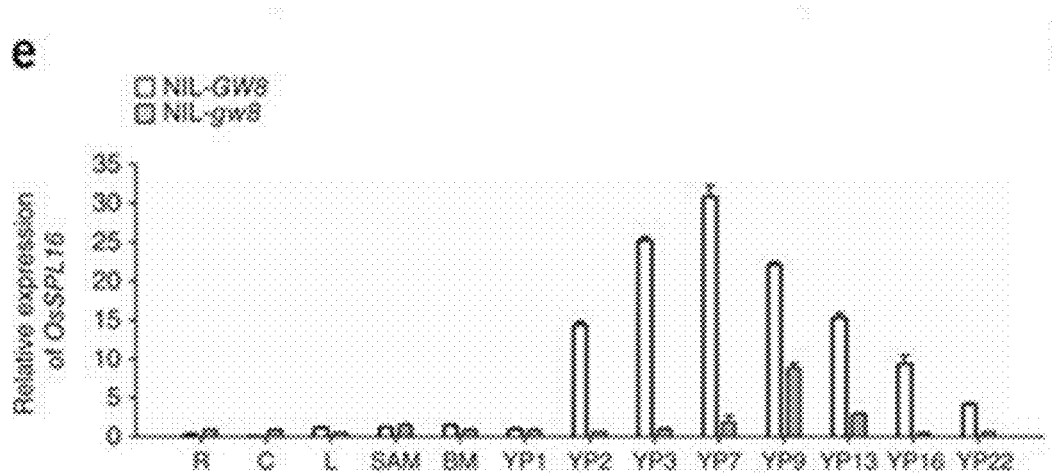

The expression profiles of OsSPL16 in various organs of HJX74 were examined by quantitative RT-PCR analysis. OsSPL16 was preferentially expressed in developing panicles, and the highest levels of OsSPL16 expression were found in panicles of 7 cm in length, whereas there was less transcript accumulation in the root, culm, leaf sheath, shoot meristem and young panicle (of <1 cm in length) (FIG. 9e). β-glucuronidase (GUS) expression was mainly in the stamen and spikelet hulls in transgenic HJX74 plants carrying the pOsSPL16::GUS reporter construct. The levels of mRNA transcript for OsSPL16 at the reproductive stage in NIL-gw8 plants were significantly lower than those in NIL-GW8 plants ($P<0.0001$) (FIG. 9e). These results indicate that the associated polymorphism is the 10-bp deletion in the OsSPL16 promoter region.

Figure 9F:
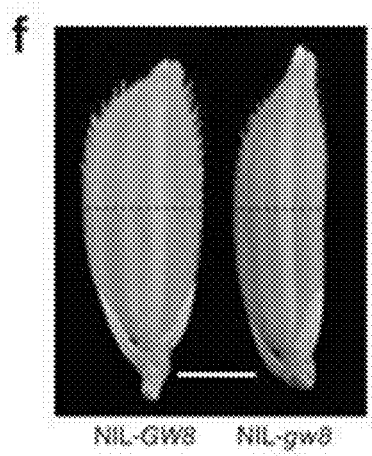
Figure 9G:
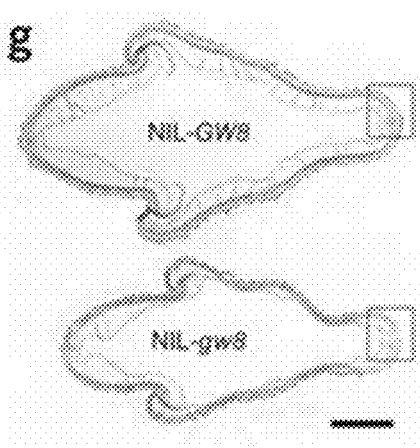
Figure 9H:
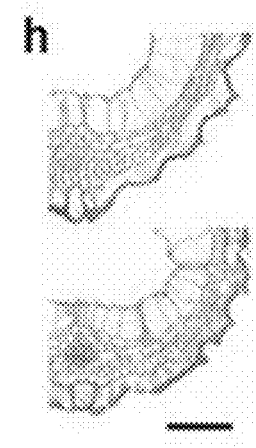
Figures 9I, 9J, 9K:
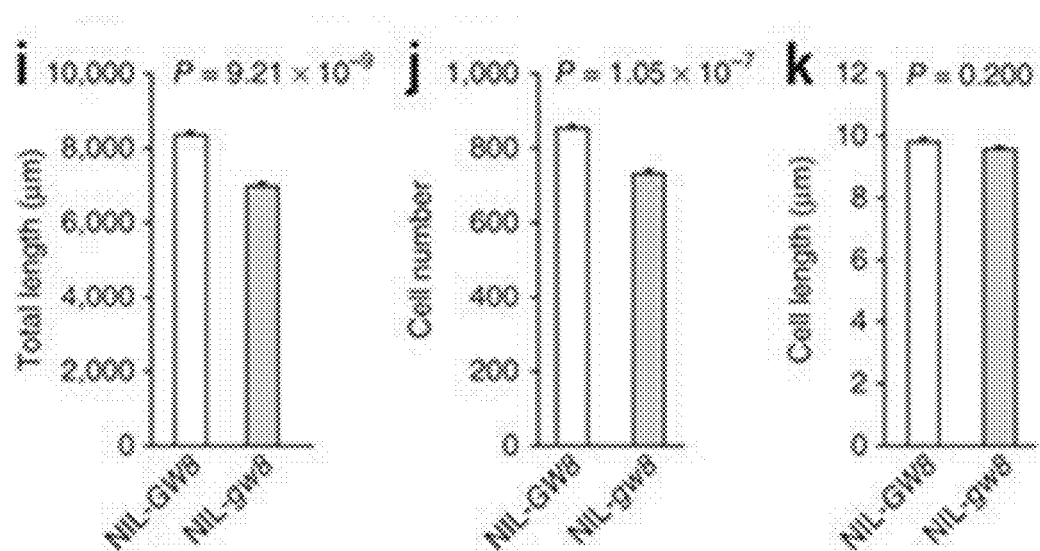

The spikelet hulls of NIL-GW8 plants were wider than those of NIL-gw8 plants before fertilization (FIG. 9f). There was little, if any, difference in cell length in either the palea or the lemma, but the cells in the outer parenchyma cell layer of NIL-GW8 hulls were 19.5% longer and contained 18.1% more cells than their equivalents in NIL-gw8 hulls (FIG. 9g-k). Inspection of longitudinal palea and lemma sections showed that cells in the NIL-gw8 inner parenchyma cell layer were 6.5% longer than equivalent NIL-GW8 cells. These observations indicate that qGW8 might promote latitudinal growth by increasing cell proliferation and inhibit longitudinal growth by repressing cell elongation.

The effect of the allele makeup at qGW8 on grain yield was tested in field-grown rice. The two NILs did not differ from one another with respect to plant or panicle architecture, but their grain sizes were clearly distinct (FIG. 10a-g). The width of the NIL-GW8 grain was 14.9% greater and its length 6.9% less than the corresponding measures in NIL-gw8 plants (FIG. 10h,i); this generated a 13.9% advantage for NIL-GW8 with respect to 1,000-grain weight (FIG. 10j) and a 14.3% advantage in plot grain yield (from 40 plants) across two locations over a 3-year period (FIG. 10k and Table 2). Because large spikelet hulls can be associated with incomplete grain filling5, the fresh

TABLE 2

Yield test in paddies among NIL-GW8, NIL-gw8 and NIL-gw8$^{Amol}$ plants.

| | Actual yield per plot (Kg) in 2008$^{\Psi}$ | Actual yield per plot (Kg) in 2009$^{\Psi}$ | Actual yield per plot (Kg) in 2010$^{\Psi}$ |
|---|---|---|---|
| Hainan | | | |
| NIL-GW8 | 1.10 ± 0.02 bB¶ | 1.09 ± 0.07 bB | 1.19 ± 0.02 bB |
| NIL-gw8§ | 1.01 ± 0.01 aA | 0.99 ± 0.01 aA | 1.03 ± 0.02 aA |
| NIL-gw8$^{Amol}$* | 1.09 ± 0.02 bB | 1.06 ± 0.02 bAB | 1.12 ± 0.04 bB |
| Beijing | | | |
| NIL-GW8 | 1.17 ± 0.02 bB | 1.21 ± 0.01 cB | 1.28 ± 0.02 cB |
| NIL-gw8§ | 1.03 ± 0.01 aA | 1.03 ± 0.01 aA | 1.05 ± 0.02 aA |
| NIL-gw8$^{Amol}$* | 1.17 ± 0.02 bB | 1.07 ± 0.01 bA | 1.24 ± 0.01 bB |

$^{\Psi}$Data given as mean ± SE (n = 40). Plants were grown in randomized complete block (each block contain 10 plots, and each plots contains 40 plants) design with 4 replications, respectively.
§Multiway ANOVA revealed a significant difference in grain yield between NIL-GW8 and NIL-gw8 plants (P < 0.05), and this effect was consistent across 3 years and across 2 locations.
*Multiway ANOVA showed no significant differences in grain yield between NIL-GW8 and NIL-gw8$^{Amol}$ plants (P < 0.01), except Beijing in 2009.
¶Values in the same column with the same letters do not differ significantly, the values with different subscript letter differ significantly (with small letter, P < 0.05) or very significantly (with capital letter, P < 0.01).

and dry weights of endosperm from the NIL-GW8 and NIL-gw8 grains were compared. When measured 15 d after anthesis, both the fresh and dry endosperm weights of NIL-GW8 grains were significantly greater than those of the NIL-gw8 grains (P<0.0001); these differences peaked at ~21 d after anthesis.

Example 3—Cloning of the Rice Grain Width, Grain Weight Gene GW8/OsSPL16

Fine mapping was carried out using 2,000 BC2F2 progeny bred from the cross between an SSSL (W09-38-60-7-7) and HJX74. Genotyping at the two molecular markers RM447 and RM502 was used to identify a set of individuals that were homozygous with respect to qgw8. The genomic location of the QTL was then refined by genotyping the progeny of these individuals with a set of de novo markers known to lie in the relevant genomic region. Candidate gene identification in the critical genomic segment relied on comparisons between the local genomic sequences of Basmati385 and HJX74.

A localized high-resolution map constructed on the basis of the analysis of 2,000 F2 segregants allowed the placement of qGW8 between RM502 and PSM736 (FIG. 8c). The progeny testing of homozygous recombinant plants allowed this region to be narrowed to ~7.5-kb stretch flanked by RM502 and PSM711 (FIG. 8d), a segment that contains only the promoter region and the predicted first exon of the LOC_Os08g41940 ORF. The candidate gene OsSPL16 encodes a squamosa promoter-binding protein-like 16, which belongs to the SBP domain family of transcription factors and shares homology with the product of tga1, a domestication syndrome gene associated with the formation of naked grains in maize. Sequence comparison of OsSPL16 in HJX74 and Basmati385 revealed six polymorphisms: a 10-bp indel in the promoter region (c.-32_-23delGAGCT-GAGCT), an in-frame 3-bp indel in exon 1 (c.327_328insGCG), one synonymous polymorphism (c.36T>C) and three missense polymorphisms (c.236T>C, c.818A>C and c.1089T>G) (FIG. 8e).

Example 4—Rice Grain Width, Grain Weight and Yield of GW8 Variants

The present disclosure utilizes the wide grain width line (Huajingxian 74, between 2.65-2.75 mm) with the narrow particle Basmati385 (grain width ranging from 2.15-2.25 mm) to construct chromosomal single-segment substitution lines of mapping populations. Map-based cloning was performed as described herein to the GW8 genes, to isolate the genomic DNA sequence of the gene (GW8 gDNA) as shown in SEQ ID NO: 4 shows. The GW8 gene contains two introns. The cDNA sequences shown in SEQ ID NO: 1 encoded a protein of 454 amino acids as shown in SEQ ID NO: 9.

Comparative sequence analysis showed that the 5 nucleotide sequence differences (four base substitution mutations: T36C, T236C, A818C and T1089G), 3 bp insertion mutation exists in the coding region, three of which relates to the amino acid coding variation (specific for the C36T L236P and the 3 bp insertion mutation) The sequence differences also exist in the Huajingxian 74. The sequencing of the other wide grain SSSLs materials W06-40-48-06-02-03-02-03-1 was performed and it was inferred that amino acid variation is not the main cause of the grain width changes.

The strategy for the development of SSSLs derived from the cross between the two indica varieties Basmati385 (the donor parent) and HJX74 (the recurrent parent). To construct the library, 563 PCR-based simple sequence repeat (SSR) markers distributed evenly throughout 12 chromosomes were used for the genotyping and selection of the donor-substituted segment or non-substituted chromosomal regions. As a result, a fixed population of 153 SSSLs was generated, with each containing only one chromosome segment from the donor substituted in the HJX74 genetic background.

GW8 expression levels were analyzed in the SSSLs material analysis and by comparison, it was found that GW8 expression in young spike in the Huajingxian 74 and W06-40-48-06-02-03-02-03-1 background was significantly higher than W09-38-60-07-07-03-04-0049-16. The decreased expression level resulted in narrow W09-38-60-07-07-03-04-0049-16-grain type.

Example 5—The Marker-Assisted Selection Breeding Experiments Involving GW8

GW8 internal PCR oligonucleotide primers (SEQ ID NO: 12 and SEQ ID NO: 13) were designed and PCR using Taq DNA polymerase was performed for amplification of the wide particulate material along with a narrow particle material (e.g. Huajingxian 74 and W02-15-01-08-14-05-01-32 CSSLs). The difference in DNA can be detected through a 6% polyacrylamide and/or 4% agrose gel electrophoresis caused by 10-bp insertion. The results show that wide-grain variety has a slightly larger band that was used to specifically identify the wide variety versus the narrow variety using molecular markers. Groups in the large grain varieties and the arabica varieties of hybrid offspring that can be used to filter out the mark quickly offspring carry a wide grain gene material.

GW8 internal PCR oligonucleotide primers (SEQ ID NO: 46 and SEQ ID NO: 47) were designed to detect the elite gw8$^{Amol}$ allele caused by CT insertion in the coding region of OsSPL16 using PCR amplification, which were effectively used to control grain size and simultaneously improve grain quality and yield.

Example 6—Rice Transgenic Experiments

Three constructs were made (pActin::RNAi-OsSPL16, pOsSPL16::OsSPL16$^{HJX74}$ and pOsSPL16::OsSPL16$^{Basmati385}$) as described above and were used for Agrobacterium-mediated transformation. In total, about 20 independent transgenic HJX74 (NIL-GW8) plants carrying the pActin::RNAi-OsSPL16 construct (FIG. 9a), 29 independent transgenic NIL-gw8 plants carrying the pOsSPL16::OsSPL16HJX74 construct (FIG. 9b), 27 independent transgenic NIL-gw8 plants carrying the pOsSPL16::OsSPL16$^{Basmati385}$ construct (FIG. 9c) and 22 independent transgenic Basmati385 plants carrying the pOsSPL16::OsSPL16$^{Basmati385}$ construct (FIG. 9d) were obtained. The transcriptional levels of OsSPL16 in the independent transgenic lines were assessed using young panicles of 6 cm in length. Quantitative RT-PCR analysis showed that expression of OsSPL16 in the transgenic lines carrying the pOsSPL16::OsSPL16$^{HJX74}$ or pOsSPL16::OsSPL16$^{Basmati385}$ construct was significantly enhanced compared to the level in non-transgenic plants, whereas the constitutive expression of an siRNA directed against OsSPL16 caused the down-regulation of OsSPL16.

Although there were no visible changes in phenotype with respect to whole-plant type, the transgenic HJX74 plants carrying the pActin::RNAi-OsSPL16 construct formed grains that were more slender than those formed by non-transgenic HJX74 plants. In contrast, NIL-gw8 plants expressing HJX74 or Basmati385 OsSPL16 cDNA formed grains that were shorter and wider than those formed by non-transgenic NIL-gw8 plants. In addition, the transgenic Basmati385 plants expressing the Basmati385 OsSPL16 cDNA formed grains that were shorter and wider than those formed by non-transgenic Basmati385 plants. These results indicated a coordinated relationship between the transcriptional level of OsSPL16 and grain width.

OsSPL16 contains an OsmiR156 target sequence (FIG. 11f). The transgenic overexpression of OsmiR156 was shown to repress OsSPL16 transcription in young panicles. An allelic (c.1007_1008insCT) variant found in the rice cultivar Amol3 (Sona) has a 2-bp indel at the miR156 target site in OsSPL16 (FIG. 11f). This cultivar was therefore used to breed NIL-gw8$^{Amol}$, a line that contains a very short chromosome segment inherited from Amol3 in the HJX74 genetic background. Expression analysis showed that, during the reproductive stage, the expression of OsSPL16 was higher in NIL-gw8$^{Amol}$ than in NIL-GW8 plants (FIG. 11g), whereas genetic complementation analysis in which we generated transgenic NIL-gw8$^{Amol}$ plants expressing Amol3 OsSPL16 or HJX74 OsSPL16 cDNA showed that the gw8$^{Amol}$ allele functions as a loss-of-function mutation. NIL-gw8$^{Amol}$ plants formed particularly slender grains (FIG. 11h,i). There were no substantive differences in the transcript levels of genes determining panicle branching in NIL-GW8 and NIL-gw8$^{Amol}$ plants; however, NIL-gw8$^{Amol}$ plants developed more grains than NIL-GW8 plants (FIG. 11j). In contrast, transgenic plants overexpressing OsSPL16 developed less panicle branches. These results indicate that OsSPL16 functions as a negative regulator of panicle branching.

Under field conditions, the grain yield of NIL-gw8$^{Amol}$ and NIL-GW8 plants was indistinguishable (FIG. 11k and Table 2). In terms of the number of grains set per panicle, however, NIL-gw8$^{Amol}$ plants were 13.5% more productive than NIL-GW8 plants (FIGS. 10g and 11j). The gw8$^{Amol}$ allele was associated with about ~14% increase in the grain yield per plant relative to plants carrying the Basmati qgw8 allele (FIGS. 10h-k and 11i-k). The inference is that, in Basmati rice, the qgw8$^{Amol}$ allele promotes panicle branching and thereby enhances grain yield. Coordinated regulation of grain size and yield and facilitates the process of simultaneously improving grain quality and productivity in rice.

DNA fragments of the 2 kb upstream of the OsSPL16 transcription start site and the 1 kb downstream of its termination site were amplified from HJX74 plants and cloned into the binary pCAMBIA1300 vector to generate pOsSPL16::3′ UTR. The full-length OsSPL16 coding sequence was amplified from young panicles of both Basmati385 and HJX74 plants and cloned into either pOsSPL16::3′ UTR or pUbi::nos26. A 311-bp fragment of OsSPL16 cDNA was used to construct the pActin::RNAi-OsSPL16 transgene. For the pOsSPL16::GUS vector, the DNA fragment containing the OsSPL16 promoter was inserted into pCAMBIA1301-GUS-nos. The pCaMV35S::OsSPL16-GFP construct comprised a fusion between GFP amplified from the pMCB30 plasmid and OsSPL16 inserted into pCaMV35S::nos. Transgenic rice plants were generated by Agrobacterium-mediated transformation According to the GW8 cDNA sequence, primers were designed—the RNAi-BamH IF: 5′-CGGGATCCCAG-GAGTTTGATGAGGCCAAG-3 and RNAi-XbaIR: 5′-GCTCTAGA AAGCTGATCTCGCCTTCCTGG-3′. The GW8 length cDNA was used as a template to amplify a portion of the GW8 gene along the C-terminal 311 bp of sequence. The fragments were inserted into the opposite direction of GW8 cDNA fragment of the gene such plasmid pUCCRNAi.

Expression of GW8 in transgenic positive plants decreased significantly. Agronomic traits such as plant height, heading and ear type transgenic plants did not change significantly, but the transgenic rice had significant change in grain narrowing, variable length (as shown in FIG. 7). In the NIL-gw8 context, overexpression GW8 the gene caused grain widening (FIG. 6). This demonstrates that through appropriate regulation of the GW8 gene expression, rice phenotype such as grain width, aspect ratio, and grain weight, were changed and affects yield.

Example 7: Nuclear Localization of OsSPL16 and Functional Characterization

The nuclear localization of an OsSPL16-green fluorescent protein (GFP) fusion protein was consistent with the notion that OsSPL16 is a putative transcription factor, and a transcriptional activation assay showed that the activation domain is located at the N terminus of OsSPL16. Because of this indicated role for OsSPL16, the transcriptional levels of genes that have been previously shown to act as grain-size regulators (for example, GW2 and GS3) were examined. No significant difference was found in the transcript levels of these genes in NIL-GW8 and NIL-gw8 plants. It was examined whether OsSPL16 affected the expression of the key genes determining cell cycle time. The mRNA transcript levels of genes involved in the G1-to-S transition, such as CDKA1, CYCD3 and E2F2, were considerably higher in NIL-GW8 plants relative to NIL-gw8 plants. In contrast, transcripts of genes involved in the G2-to-M transition, such as CDKB, CYCB2.1 and CYCB2.2, were not upregulated in NIL-GW8 plants. Furthermore, 7-d-old Arabidopsis thaliana seedlings overexpressing the HJX74 OsSPL16 cDNA under the control of a maize ubiquitin promoter (Ubi) developed larger cotyledons and longer roots than wild-type seedlings; larger cotyledons were due mainly to greater pavement cell number rather than larger cell size, whereas longer roots reflected a larger population of root meristematic cells. These results show that OsSPL16 contributes to organ size through its effect on the cell cycle machinery.

The SPL genes have an important role in the control of flowering. The regulatory role of OsSPL16 in promoting flowering in transgenic A. thaliana plants was examined. When taking both leaf number and chronological time into account, the overexpression of OsSPL16 accelerated flowering and promoted expression of SPL-targeted MADS box genes, such as SOC1 and AGL42. Although the transgenic rice carrying a pUbi::OsSPL16 construct showed early flowering, the field-grown NIL-GW8 and NIL-gw8 plants did not differ from one another with respect to heading date.

The upregulation of OsSPL14 has been shown to promote panicle branching and plant height, as well as vascular bundle number. In contrast, the HJX74 plants that constitutively overexpressed OsSPL16 were dwarfed, formed fewer panicle branches and grains and developed abnormal glume architecture. The uppermost internode length was shorter and vascular bundle number was smaller in transgenic lines, and the shortened internode was a result of shorter cell length.

The disclosure has been described with reference to various specific and preferred embodiments and techniques. However, it should be understood that many variations and modifications may be made while remaining within the spirit and scope of the disclosure.

What is claimed is:

1. A method of improving grain width to length ratio or yield of a rice plant, the method comprising: reducing the expression of an endogenous polynucleotide encoding an amino acid sequence comprising SEQ ID NO: 9 or an amino acid sequence that is at least 95% identical to SEQ ID NO: 9, wherein the endogenous polynucleotide encodes a polypeptide involved in the regulation of the grain width to length ratio or yield, and the expression is reduced by a heterologous polynucleotide, wherein the heterologous polynucleotide comprises a fragment of SEQ ID NO: 1 that is sufficient to down-regulate the endogenous expression of the endogenous polynucleotide through RNA interference; thereby reducing the grain width of the rice plant in relation to a control plant not expressing the polynucleotide and improving the grain width to length ratio or yield of the rice plant that has reduced expression of the endogenous polynucleotide.

2. A method of increasing the length to width ratio of rice grain, the method comprising: reducing the expression of a polynucleotide that encodes a polypeptide comprising the amino acid sequence of SEQ ID NO: 9 or an allelic variant thereof that is at least 95% identical to SEQ ID NO: 9, wherein the expression is reduced by a targeted mutation of a miRNA156 target site of OsSPL16, and the width of the rice grain is reduced in relation to a control plant not expressing the polynucleotide, thereby increasing the length to width ratio.

* * * * *